US007906309B2

(12) United States Patent
Emalfarb et al.

(10) Patent No.: US 7,906,309 B2

(45) **Date of Patent: *Mar. 15, 2011**

(54) EXPRESSION-REGULATING SEQUENCES AND EXPRESSION PRODUCTS IN THE FIELD OF FILAMENTOUS FUNGI

(75) Inventors: Mark Aaron Emalfarb, Jupiter, FL (US); Peter Jan Punt, Houten (NL); Cornelia Maria Johanna Van Zeijl, Vleuten de Meern (NL)

(73) Assignee: Dyadic International (USA), Inc., Jupiter, FL (US)

( * ) Notice: Subject to any disclaimer, the term of this patent is extended or adjusted under 35 U.S.C. 154(b) by 949 days.

This patent is subject to a terminal disclaimer.

(21) Appl. No.: 10/257,629

(22) PCT Filed: Apr. 17, 2001

(86) PCT No.: PCT/NL01/00301

§ 371 (c)(1), (2), (4) Date: Apr. 11, 2003

(87) PCT Pub. No.: WO01/79507

PCT Pub. Date: Oct. 25, 2001

(65) Prior Publication Data

US 2003/0187243 A1 Oct. 2, 2003

Related U.S. Application Data

(63) Continuation-in-part of application No. 09/548,938, filed on Apr. 13, 2000, now Pat. No. 6,573,086, which is a continuation-in-part of application No. PCT/NL99/00618, filed on Oct. 6, 1999, which is a continuation-in-part of application No. PCT/EP98/06496, filed on Oct. 6, 1998.

(30) Foreign Application Priority Data

Apr. 13, 2000 (EP) .................................... 00201343

(51) Int. Cl.

| | |
|---|---|
| ***C12N 15/56*** | (2006.01) |
| ***C12N 15/80*** | (2006.01) |
| ***C12N 9/24*** | (2006.01) |
| ***C12P 19/14*** | (2006.01) |
| *C12N 1/15* | (2006.01) |

(52) U.S. Cl. .... 435/200; 435/99; 435/252.3; 435/320.1; 536/23.2

(58) Field of Classification Search ........................ None
See application file for complete search history.

(56) References Cited

U.S. PATENT DOCUMENTS

| | | | | |
|---|---|---|---|---|
| 5,457,046 A * | 10/1995 | Woldike et al. | ............... | 435/209 |
| 5,686,593 A * | 11/1997 | Woldike et al. | .............. | 536/23.1 |
| 5,763,254 A | 6/1998 | Wöldike et al. | ............... | 435/209 |
| 6,015,707 A * | 1/2000 | Emalfarb et al. | ............. | 435/263 |
| 6,121,034 A * | 9/2000 | Laroche et al. | ............... | 435/209 |
| 6,573,086 B1 * | 6/2003 | Emalfrab et al. | ........ | 435/254.11 |
| 2003/0157595 A1 * | 8/2003 | Emalfarb et al. | ............ | 435/69.1 |

FOREIGN PATENT DOCUMENTS

| | | |
|---|---|---|
| WO | WO 97/13853 | 4/1997 |
| WO | WO 97/27363 | 7/1997 |
| WO | WO 98/15633 | 4/1998 |
| WO | WO 00/20555 | 4/2000 |
| WO | WO 01/25468 A1 * | 4/2001 |

OTHER PUBLICATIONS

Seffernick et al., 2001, "Melamine deaminase and atrazine chlorohydrolase: 98 percent identical but functionally different", Journal of Bacteriology, vol. 183, No. 8, pp. 2405-2410.*

Henrissat, B., et al., 1993, "New families in the classification of glycosyl hydrolases based on amino acid sequence similarities", Biochemical Journal, vol. 293, pp. 781-788.*

Derewenda, U., et al., 1994, "Crystal structure, at 2.6-A resolution, of the Streptomyces lividans xylanase A, a member of the F family of β-1,4-D-glycanases", The Journal of Biological Chemistry, vol. 269, No. 33, pp. 20811-20814.*

K.E. Eriksson et al., "Extracellular Enzyme System Utilized by the Fungus *Sporotrichum pulverulentum* (*Chrysosporium lignorum*) for the Breakdown of Cellulose," *Eur. J. Biochem*., 51:193-206, 1975.

H. Iikura et al., "Cloning of a Gene Encoding a Putative Xylanase with a Cellulose-Binding Domain from *Humicola grisea*," *Biosci. Biotech. Biochem*., 61(9):1593-1595, 1997.

M. C. Ruiz-Roldan et al, "*Fusarium oxysporum f.* sp. *lycopersici*. family F xylanase (XYL3)," SWALL 'Online Abstract, accession No. o59937, created Aug. 1, 1998.

P. O. Sheppard et al., "The use of conserved cellulase family-specific sequences to clone cellulase homologue cDNAs from *Fusarium oxysporum*," *Gene*, 150:163-167, 1994. Accompanied by EMBL 'Online! Abstract, accession No. p46239 retrieved Jul. 31, 2003.

S. Takashima et al., "Cloning, sequencing, and expression of the cellulase genes of *Humicola grisea* var. *thermoidea*," *J. of Biotech*., 50:137-147, 1996. Accompanied by EMBL 'Online! Abstract, accession No. D63515, unpublished, retrieved Jul. 31, 2003.

Agency Response Letter GRAS Notice No. GRN 000292 (Sep. 29, 2009) from Mitchell A. Cheeseman, Acting Director; hyper text transfer protocol://www.fda.gov.

* cited by examiner

*Primary Examiner* — Nashaat T Nashed
*Assistant Examiner* — William W Moore
(74) *Attorney, Agent, or Firm* — McDermott, Will & Emery; Michael J. Keller; Nicole R. Sullivan

(57) ABSTRACT

The invention pertains to novel proteins corresponding to *Chrysosporium* glycosyl hydrolases of families 7 and 10, exhibiting a minimum aminoacid identity of 70 and 75%, respectively, with the amino acid sequence of SEQ ID No's 2 and 4, and to a protein corresponding to a *Chrysosporium* glyceraldehyde phosphate dehydrogenase, exhibiting at least 86% amino acid identity with the partial amino acid sequence of SEQ ID No. 6. The invention further relates to nucleic acid sequences encoding these proteins, and especially to promoter sequences regulating the expression of the corresponding genes. The preferred host for expressing these genes is a fungus, especially a *Chrysosporium* strain.

9 Claims, 2 Drawing Sheets

SEQUENCE LISTING

<160> NUMBER OF SEQ ID NOS: 12

<210> SEQ ID NO 1
<211> LENGTH: 4451
<212> TYPE: DNA
<213> ORGANISM: Chrysosporium lucknowense
<220> FEATURE:
<221> NAME/KEY: CDS
<222> LOCATION: (1780)..(2188)
<220> FEATURE:
<221> NAME/KEY: CDS
<222> LOCATION: (2256)..(3424)
<220> FEATURE:
<221> NAME/KEY: modified_base
<222> LOCATION: (2941)
<223> OTHER INFORMATION: a, t, c, g, other or unknown

<400> SEQUENCE: 1

```
aaggtatccg atttggggaa cgtcgatgaa agtattgcaa aagtgacgag agttgcgcaa     60

ctaactcgct gccgaagaag ctgcggaaga aagagaacac cgaaagtgga ataacgttac    120

ggatgtcctg acctcaaagt tgaaaccagc ccttcctgct ctatttggga aagcggcttg    180

cccttgaatg cgctgcactg tggcacgact accagtgatc gggaggagca aactaccctg    240

gtccgttcct tggtggggcg gcactaggcc caacttaggg tgatcggagg tcgatgccgc    300

ggtcctcgtt ggtctgggct cttctcattt cccggtttgc accccccgtt gcacctgctg    360

atcgcccgcc aacgccgatg aggttgcgcc cagaccgaca atcaccgcgg ctgcattccc    420

aagtatattg aagatggcac caggtacccg gttttgcgtc ccagtcgttt ggtgccaaat    480

ttgggagttt ttgagcctca agatctgggg aaatcgacct caacttccat acaagttaaa    540

gtcgcacaca cggcgagttc cacgaagaga cacatttttt tctgaaggcc tctctccccg    600

cacatcagaa accaccaaat accaagactg cagaagccgg ggtaagtggg ccaccgggac    660

tacactaaaa tgcggggaga agcgagatcc gttgcgaagg gaagggatgg ggtgtgctgc    720

ggctttctcc gctctcgtgc gccttttgct tgaatctagt gtacaccagg gtaggctccg    780

aaggagtatc tacggcagcg ctgttcgtgc tgcgttgaga gtcagggcgg agacgagcag    840

gcgacaggag cctcgcaccg gcacttcgga tcgcatttgc gcggagcgtc aaatacgctc    900

ttctgcggtc atcagagagc atcgtgaacc aaggttcttc cgcagggcgg cctgggcttc    960

gcagagtcgc actcggcgga cgccttccgt gtcaccccctg ataacctggc tgccgcgccc   1020

agactcctcc aatgaggtgt gtggttgccc tcgccgaccc ttcagcaacc ttaatcgctt   1080

ccatcgcacg gctccacgtc ctcgaacgat gccctcagtc cgtgcccggc cgtggcaacc   1140

ataacgtgac atcgccgccc agcctactag ccgctatcga ccggttaggc ttgtcaccgc   1200

agcgcccatt ctccatcggg cctctactct gatccacctc acccaccgca agcactagcg   1260

agcctcacca gagtgcaagc gacacgaccc gcttggccct tcgtccttga ctatctccca   1320

gacctcttgc catcttgccg acgccgcccc cttttttttc tcctccccct gccggcaggt   1380

cggtggcccc agtcccgaga tggcattgct ccgttgtcca tgacgaccca tcattcgatg   1440

gctgactggc acactcgtct tgtttgagca tcgacggccc gcggcccgtc tcccacggta   1500

cggaacctcg ttgtacagta cctctcgtaa tgatacccaa caccggggcc gagcgctggg   1560

agggcggcgt tcccgagaag ccgggaaggc ggctggccgg ctgacctttg tgacttggcg   1620

atggatgcgg ccatggagaa tgtccgtccg aagcgacgcg acaattagcc tggctaccat   1680

cgatataaat tgggtgattc ccagctcttg atgggcgtgt cttctgcctg gcagccctcg   1740
```

-continued

```
tcttcagatc aagcaactgt gtgctgatcc tcttccgcc atg tac gcc aag ttc      1794
                                           Met Tyr Ala Lys Phe
                                             1               5

gcg acc ctc gcc gcc ctt gtg gct ggc gcc gct gct cag aac gcc tgc      1842
Ala Thr Leu Ala Ala Leu Val Ala Gly Ala Ala Ala Gln Asn Ala Cys
                 10                  15                  20

act ctg acc gct gag aac cac ccc tcg ctg acg tgg tcc aag tgc acg      1890
Thr Leu Thr Ala Glu Asn His Pro Ser Leu Thr Trp Ser Lys Cys Thr
             25                  30                  35

tct ggc ggc agc tgc acc agc gtc cag ggt tcc atc acc atc gac gcc      1938
Ser Gly Gly Ser Cys Thr Ser Val Gln Gly Ser Ile Thr Ile Asp Ala
         40                  45                  50

aac tgg cgg tgg act cac cgg acc gat agc gcc acc aac tgc tac gag      1986
Asn Trp Arg Trp Thr His Arg Thr Asp Ser Ala Thr Asn Cys Tyr Glu
     55                  60                  65

ggc aac aag tgg gat act tcg tac tgc agc gat ggt cct tct tgc gcc      2034
Gly Asn Lys Trp Asp Thr Ser Tyr Cys Ser Asp Gly Pro Ser Cys Ala
 70                  75                  80                  85

tcc aag tgc tgc atc gac ggc gct gac tac tcg agc acc tat ggc atc      2082
Ser Lys Cys Cys Ile Asp Gly Ala Asp Tyr Ser Ser Thr Tyr Gly Ile
                 90                  95                 100

acc acg agc ggt aac tcc ctg aac ctc aag ttc gtc acc aag ggc cag      2130
Thr Thr Ser Gly Asn Ser Leu Asn Leu Lys Phe Val Thr Lys Gly Gln
            105                 110                 115

tac tcg acc aac atc ggc tcg cgt acc tac ctg atg gag agc gac acc      2178
Tyr Ser Thr Asn Ile Gly Ser Arg Thr Tyr Leu Met Glu Ser Asp Thr
        120                 125                 130

aag tac cag a gtaagttcct ctcgcacccg gccgccggga gatgatggcg           2228
Lys Tyr Gln
    135

cccagcccgc tgacgcgaat gacacag tg ttc cag ctc ctc ggc aac gag ttc    2281
                             Met Phe Gln Leu Leu Gly Asn Glu Phe
                                         140                 145

acc ttc gat gtc gac gtc tcc aac ctc ggc tgc ggc ctc aat ggc gcc      2329
Thr Phe Asp Val Asp Val Ser Asn Leu Gly Cys Gly Leu Asn Gly Ala
                150                 155                 160

ctc tac ttc gtg tcc atg gat gcc gat ggt ggc atg tcc aag tac tcg      2377
Leu Tyr Phe Val Ser Met Asp Ala Asp Gly Gly Met Ser Lys Tyr Ser
            165                 170                 175

ggc aac aag gca ggt gcc aag tac ggt acc ggc tac tgt gat tct cag      2425
Gly Asn Lys Ala Gly Ala Lys Tyr Gly Thr Gly Tyr Cys Asp Ser Gln
        180                 185                 190

tgc ccc cgc gac ctc aag ttc atc aac ggc gag gcc aac gta gag aac      2473
Cys Pro Arg Asp Leu Lys Phe Ile Asn Gly Glu Ala Asn Val Glu Asn
    195                 200                 205

tgg cag agc tcg acc aac gat gcc aac gcc ggc acg ggc aag tac ggc      2521
Trp Gln Ser Ser Thr Asn Asp Ala Asn Ala Gly Thr Gly Lys Tyr Gly
210                 215                 220                 225

agc tgc tgc tcc gag atg gac gtc tgg gag gcc aac aac atg gcc gcc      2569
Ser Cys Cys Ser Glu Met Asp Val Trp Glu Ala Asn Asn Met Ala Ala
                230                 235                 240

gcc ttc act ccc cac cct tgc acc gtg atc ggc cag tcg cgc tgc gag      2617
Ala Phe Thr Pro His Pro Cys Thr Val Ile Gly Gln Ser Arg Cys Glu
            245                 250                 255

ggc gac tcg tgc ggc ggt acc tac agc acc gac cgc tat gcc ggc atc      2665
Gly Asp Ser Cys Gly Gly Thr Tyr Ser Thr Asp Arg Tyr Ala Gly Ile
        260                 265                 270

tgc gac ccc gac gga tgc gac ttc aac tcg tac cgc cag ggc aac aag      2713
Cys Asp Pro Asp Gly Cys Asp Phe Asn Ser Tyr Arg Gln Gly Asn Lys
    275                 280                 285
```

-continued

```
acc ttc tac ggc aag ggc atg acg gtc gac acg acc aag aag atc acg     2761
Thr Phe Tyr Gly Lys Gly Met Thr Val Asp Thr Thr Lys Lys Ile Thr
290                 295                 300                 305

gtc gtc acc cag ttc ctc aag aac tcg gcc ggc gag ctc tcc gag atc     2809
Val Val Thr Gln Phe Leu Lys Asn Ser Ala Gly Glu Leu Ser Glu Ile
                310                 315                 320

aag cgg ttc tac gtc cag aac ggc aag gtc atc ccc aac tcc gag tcc     2857
Lys Arg Phe Tyr Val Gln Asn Gly Lys Val Ile Pro Asn Ser Glu Ser
            325                 330                 335

acc atc ccg ggc gtc gag ggc aac tcc atc acc cag gac tgg tgc gac     2905
Thr Ile Pro Gly Val Glu Gly Asn Ser Ile Thr Gln Asp Trp Cys Asp
        340                 345                 350

cgc cag aag gcc gcc ttc ggc gac gtg acc gac ttn cag gac aag ggc     2953
Arg Gln Lys Ala Ala Phe Gly Asp Val Thr Asp Xaa Gln Asp Lys Gly
    355                 360                 365

ggc atg gtc cag atg ggc aag gcc ctc gcg ggg ccc atg gtc ctc gtc     3001
Gly Met Val Gln Met Gly Lys Ala Leu Ala Gly Pro Met Val Leu Val
370                 375                 380                 385

atg tcc atc tgg gac gac cac gcc gtc aac atg ctc tgg ctc gac tcc     3049
Met Ser Ile Trp Asp Asp His Ala Val Asn Met Leu Trp Leu Asp Ser
                390                 395                 400

acc tgg ccc atc gac ggc gcc ggc aag ccg ggc gcc gag cgc ggt gcc     3097
Thr Trp Pro Ile Asp Gly Ala Gly Lys Pro Gly Ala Glu Arg Gly Ala
            405                 410                 415

tgc ccc acc acc tcg ggc gtc ccc gct gag gtc gag gcc gag gcc ccc     3145
Cys Pro Thr Thr Ser Gly Val Pro Ala Glu Val Glu Ala Glu Ala Pro
        420                 425                 430

aac tcc aac gtc atc ttc tcc aac atc cgc ttc ggc ccc atc ggc tcc     3193
Asn Ser Asn Val Ile Phe Ser Asn Ile Arg Phe Gly Pro Ile Gly Ser
    435                 440                 445

acc gtc tcc ggc ctg ccc gac ggc ggc agc ggc aac ccc aac ccg ccc     3241
Thr Val Ser Gly Leu Pro Asp Gly Gly Ser Gly Asn Pro Asn Pro Pro
450                 455                 460                 465

gtc agc tcg tcc acc ccg gtc ccc tcc tcg tcc acc aca tcc tcc ggt     3289
Val Ser Ser Ser Thr Pro Val Pro Ser Ser Ser Thr Thr Ser Ser Gly
                470                 475                 480

tcc tcc ggc ccg act ggc ggc acg ggt gtc gct aag cac tat gag caa     3337
Ser Ser Gly Pro Thr Gly Gly Thr Gly Val Ala Lys His Tyr Glu Gln
            485                 490                 495

tgc gga gga atc ggg ttc act ggc cct acc cag tgc gag agc ccc tac     3385
Cys Gly Gly Ile Gly Phe Thr Gly Pro Thr Gln Cys Glu Ser Pro Tyr
        500                 505                 510

act tgc acc aag ctg aat gac tgg tac tcg cag tgc ctg taaacgaacc      3434
Thr Cys Thr Lys Leu Asn Asp Trp Tyr Ser Gln Cys Leu
    515                 520                 525

tctctgaagg aggttctgag acacgcgcga ttcttctgta tatagtttta tttttcactc   3494

tggagtgctt cgctccacca gtacataaac cttttttttc acgtaacaaa atggcttctt   3554

ttcagaccat gtgaaccatc ttgatgcctt gacctcttca gttctcactt taacgtagtt   3614

cgcgttagtc tgtatgtccc agttgcatgt agttgagata aataccccctg gaagtgggtc   3674

tgggcctttg tgggacggag ccctctttct gtggtctgga gagcccgctc tctaccgcct   3734

accttcttac cacagtacac tactcacaca ttgctgaact gacccatcat accgtacttt   3794

atcctgttaa ttcgtggtgc tgtcgactat tctatttgct caaatggaga gcacattcat   3854

cggcgcaggg atacacggtt tatggacccc aagagtgtaa ggactattat tagtaatatt   3914

atatgcctct aggcgcctta acttcaacag gcgagcacta ctaatcaact tttggtagac   3974

ccaattacaa acgaccatac gtgccggaaa ttttgggatt ccgtccgctc tccccaacca   4034
```

-continued

```
agctagaaga ggcaacgaac agccaatccc ggtgctaatt aaattatatg gttcattttt   4094

tttaaaaaaa ttttttcttc ccattttcct ctcgcttttc tttttcgcat cgtagttgat   4154

caaagtccaa gtcaagcgag ctatttgtgc tatagctcgg tggctataat cagtacagct   4214

tagagaggct gtaaaggtat gataccacag cagtattcgc gctataagcg gcactcctag   4274

actaattgtt acggtctaca gaagtaggta ataaaagcgt taattgttct aaatactaga   4334

ggcacttaga gaagctatct aaatatatat tgaccctagc ttattatccc tattagtaag   4394

ttagttagct ctaacctata gatagccaaa tgctataata ggtaccaggg ttcaaaa      4451


<210> SEQ ID NO 2
<211> LENGTH: 526
<212> TYPE: PRT
<213> ORGANISM: Chrysosporium lucknowense
<220> FEATURE:
<221> NAME/KEY: MOD_RES
<222> LOCATION: (365)
<223> OTHER INFORMATION: Any amino acid

<400> SEQUENCE: 2

Met Tyr Ala Lys Phe Ala Thr Leu Ala Ala Leu Val Ala Gly Ala Ala
  1               5                  10                  15

Ala Gln Asn Ala Cys Thr Leu Thr Ala Glu Asn His Pro Ser Leu Thr
             20                  25                  30

Trp Ser Lys Cys Thr Ser Gly Gly Ser Cys Thr Ser Val Gln Gly Ser
         35                  40                  45

Ile Thr Ile Asp Ala Asn Trp Arg Trp Thr His Arg Thr Asp Ser Ala
     50                  55                  60

Thr Asn Cys Tyr Glu Gly Asn Lys Trp Asp Thr Ser Tyr Cys Ser Asp
 65                  70                  75                  80

Gly Pro Ser Cys Ala Ser Lys Cys Cys Ile Asp Gly Ala Asp Tyr Ser
                 85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285
```

```
Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Xaa Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525


<210> SEQ ID NO 3
<211> LENGTH: 3028
<212> TYPE: DNA
<213> ORGANISM: Chrysosporium lucknowense
<220> FEATURE:
<221> NAME/KEY: CDS
<222> LOCATION: (970)..(1042)
<220> FEATURE:
<221> NAME/KEY: CDS
<222> LOCATION: (1117)..(1180)
<220> FEATURE:
<221> NAME/KEY: CDS
<222> LOCATION: (1332)..(1594)
<220> FEATURE:
<221> NAME/KEY: CDS
<222> LOCATION: (1673)..(2424)
<220> FEATURE:
<221> NAME/KEY: modified_base
<222> LOCATION: (46)..(47)
<223> OTHER INFORMATION: a, t, c, g, other or unknown
<220> FEATURE:
<221> NAME/KEY: modified_base
<222> LOCATION: (374)
<223> OTHER INFORMATION: a, t, c, g, other or unknown

<400> SEQUENCE: 3

tcatcaactt ggcgtttgga tgtactaata ttacacgtcg tttgcnnagc ggagtctgtg      60

tcatctccgt ggggtcgggt gctccagacg acgcttcggg ccgatcctga attcgggaag     120

gaaacggttc ggctaatcag gtcctctaaa atataacgaa gcactacaga gggagttcct     180

cagaggacat cgtatcaacc gaagaacgaa gcgccgaaag gactgatcaa aacaggagta     240
```

-continued

```
ggtagggatg tgtgagtacc taaactttcc atacctgaca taaaatcatc atggtgcttc    300

agacctgttt gatgaggcga gggcggaggc cgcattgtat tttcgttcct tccttctttt    360

tgttagtata tctnagggtt ccatcgtaaa atggaatctt ccagctctac tagtaattag    420

aacaatagtt ctgatgtcgt gcgccaagct ttttcagatg actgccaaaa acccatcatg    480

ggtatggaca aaagcagtaa tcggagtcac aacgccgcat tttccttcat gatttccgtc    540

aaccggagag gtcggaggag gactccggcc acatgtgatg cgaagaagta catggcgcca    600

tggttctaac ctcttatagt ctgaaaatgc gcggaggcca gcgaagccaa gcccgggaac    660

cgttcttgtc atggtttcag tattgtttcg ctaaacattc tatccgattc gcgataggtg    720

cggctgccac cgaaggttgt atccttaaag ctttggtaag tacggagtac ggaaatggaa    780

acgcgccgca gtcctggttc catcggtatc ctccgcatgc tccgccaaaa aaagaaaacc    840

cgggtatgtt tacaaaggat ataagagaca agatgcacca cccgcccccct tcccatctgc   900

cggttgccca cgtcgccgtc gactgcttgt ccgcttccta cctgcagcct ctttcagaga    960

ccatcaaac atg cgt act ctt acg ttc gtg ctg gca gcc gcc ccg gtg gct   1011
          Met Arg Thr Leu Thr Phe Val Leu Ala Ala Ala Pro Val Ala
            1               5                  10

gtg ctt gcc caa tct cct ctg tgg ggc cag t gtatgtaatt gccttactcg     1062
Val Leu Ala Gln Ser Pro Leu Trp Gly Gln
 15                  20

gaaaatagtc accactagag ggacttaagc tcactacttc ctgtttcaca atag gc      1118
                                                            Cys
                                                             25

ggc ggt caa ggc tgg aca ggt ccc acg acc tgc gtt tct ggc gca gta     1166
Gly Gly Gln Gly Trp Thr Gly Pro Thr Thr Cys Val Ser Gly Ala Val
                 30                  35                  40

tgc caa ttc gtc aa gtcagtaact gcttttattt cttttctctc tgggattacg      1220
Cys Gln Phe Val Asn
            45

atttcgtttt gcacttagct tggttctgca tttcattgtt gtattgttct ctttttgtgt   1280

gtgagaggtt ttattaccac ctaaaggcca tttgctaaca aatctcccca g t gac      1335
                                                            Asp

tgg tac tcc caa tgc gtg ccc gga tcg agc aac cct cct acg ggc acc     1383
Trp Tyr Ser Gln Cys Val Pro Gly Ser Ser Asn Pro Pro Thr Gly Thr
        50                  55                  60

acc agc agc acc act gga agc acc ccg gct cct act ggc ggc ggc ggc     1431
Thr Ser Ser Thr Thr Gly Ser Thr Pro Ala Pro Thr Gly Gly Gly Gly
    65                  70                  75

agc gga acc ggc ctc cac gac aaa ttc aag gcc aag ggc aag ctc tac     1479
Ser Gly Thr Gly Leu His Asp Lys Phe Lys Ala Lys Gly Lys Leu Tyr
 80                  85                  90                  95

ttc gga acc gag atc gat cac tac cat ctc aac aac aat gcc ttg acc     1527
Phe Gly Thr Glu Ile Asp His Tyr His Leu Asn Asn Asn Ala Leu Thr
                100                 105                 110

aac att gtc aag aaa gac ttt ggt caa gtc act cac gag aac agc ttg     1575
Asn Ile Val Lys Lys Asp Phe Gly Gln Val Thr His Glu Asn Ser Leu
            115                 120                 125

aag tgg gat gct act gag c gtgagtgacc tctcctcctt ctcccgacaa          1624
Lys Trp Asp Ala Thr Glu
        130

taatagataa ttacgagccg gttcgaggct gacattgcgc gattctag cg agc cgc     1680
                                                     Pro Ser Arg
                                                         135

aat caa ttc aac ttt gcc aac gcc gac gcg gtt gtc aac ttt gcc cag     1728
Asn Gln Phe Asn Phe Ala Asn Ala Asp Ala Val Val Asn Phe Ala Gln
```

-continued

```
            140                 145                 150

gcc aac ggc aag ctc atc cgc ggc cac acc ctc ctc tgg cac tct cag     1776
Ala Asn Gly Lys Leu Ile Arg Gly His Thr Leu Leu Trp His Ser Gln
        155                 160                 165

ctg ccg cag tgg gtg cag aac atc aac gac cgc aac acc ttg acc cag     1824
Leu Pro Gln Trp Val Gln Asn Ile Asn Asp Arg Asn Thr Leu Thr Gln
    170                 175                 180

gtc atc gag aac cac gtc acc acc ctt gtc act cgc tac aag ggc aag     1872
Val Ile Glu Asn His Val Thr Thr Leu Val Thr Arg Tyr Lys Gly Lys
185                 190                 195                 200

atc ctc cac tgg gac gtc gtt aac gag atc ttt gcc gag gac ggc tcg     1920
Ile Leu His Trp Asp Val Val Asn Glu Ile Phe Ala Glu Asp Gly Ser
                205                 210                 215

ctc cgc gac agc gtc ttc agc cgc gtc ctc ggc gag gac ttt gtc ggc     1968
Leu Arg Asp Ser Val Phe Ser Arg Val Leu Gly Glu Asp Phe Val Gly
            220                 225                 230

atc gcc ttc cgc gcc gcc cgc gcc gcc gat ccc aac gcc aag ctc tac     2016
Ile Ala Phe Arg Ala Ala Arg Ala Ala Asp Pro Asn Ala Lys Leu Tyr
        235                 240                 245

atc aac gac tac aac ctc gac att gcc aac tac gcc aag gtg acc cgg     2064
Ile Asn Asp Tyr Asn Leu Asp Ile Ala Asn Tyr Ala Lys Val Thr Arg
    250                 255                 260

ggc atg gtc gag aag gtc aac aag tgg atc gcc cag ggc atc ccg atc     2112
Gly Met Val Glu Lys Val Asn Lys Trp Ile Ala Gln Gly Ile Pro Ile
265                 270                 275                 280

gac ggc atc ggc acc cag tgc cac ctg gcc ggg ccc ggc ggg tgg aac     2160
Asp Gly Ile Gly Thr Gln Cys His Leu Ala Gly Pro Gly Gly Trp Asn
                285                 290                 295

acg gcc gcc ggc gtc ccc gac gcc ctc aag gcc ctc gcc gcg gcc aac     2208
Thr Ala Ala Gly Val Pro Asp Ala Leu Lys Ala Leu Ala Ala Ala Asn
            300                 305                 310

gtc aag gag atc gcc atc acc gag ctc gac atc gcc ggc gcc tcc gcc     2256
Val Lys Glu Ile Ala Ile Thr Glu Leu Asp Ile Ala Gly Ala Ser Ala
        315                 320                 325

aac gac tac ctc acc gtc atg aac gcc tgc ctc cag gtc tcc aag tgc     2304
Asn Asp Tyr Leu Thr Val Met Asn Ala Cys Leu Gln Val Ser Lys Cys
    330                 335                 340

gtc ggc atc acc gtc tgg ggc gtc tct gac aag gac agc tgg agg tcg     2352
Val Gly Ile Thr Val Trp Gly Val Ser Asp Lys Asp Ser Trp Arg Ser
345                 350                 355                 360

agc agc aac ccg ctc ctc ttc gac agc aac tac cag cca aag gcg gca     2400
Ser Ser Asn Pro Leu Leu Phe Asp Ser Asn Tyr Gln Pro Lys Ala Ala
                365                 370                 375

tac aat gct ctg att aat gcc ttg taagaggagg tatattattt ttagaggcaa    2454
Tyr Asn Ala Leu Ile Asn Ala Leu
            380

tgaagctagg aggaaagagg ggaagtgagg taattagcta ggacaggcaa atctagcagc   2514

aattataagt caacactata taaaatattc ctataatggc ttgtgcttcg gtgtgcaaaa   2574

aaaaaaaaaa aaaaaaaaaa aaaaaaaaaa aaaaactcaa aaacaaaaat gatccaacat   2634

gattcgaaat ggcgaccttg caaatgcaca cctcagataa taccactata caatacacct   2694

taaatggcac ctaaatccat ttgtctgcgg tcatagacgg ggcttaagaa gcctgggatg   2754

caggtgtcga tgcaagggtt acgtcagtgt atgatatgag tatgaaccat gctgtctggg   2814

taattctcca ctttccctcc ccttacgact cttcgggtgt gcctctctag aaagtcgact   2874

cctggcgcct cagatcgccc tttggctctg ttcggtacaa tgacgtccgc tggtttcttc   2934

caaagaccag gtatttctcc cgtggcaaca aagaatacca aatacctata tcgaaccgta   2994
```

```
gtcttctgat aattagatgt ctctcaaggc gcgg                          3028


<210> SEQ ID NO 4
<211> LENGTH: 384
<212> TYPE: PRT
<213> ORGANISM: Chrysosporium lucknowense

<400> SEQUENCE: 4

Met Arg Thr Leu Thr Phe Val Leu Ala Ala Ala Pro Val Ala Val Leu
1               5                   10                  15

Ala Gln Ser Pro Leu Trp Gly Gln Cys Gly Gly Gln Gly Trp Thr Gly
            20                  25                  30

Pro Thr Thr Cys Val Ser Gly Ala Val Cys Gln Phe Val Asn Asp Trp
        35                  40                  45

Tyr Ser Gln Cys Val Pro Gly Ser Ser Asn Pro Pro Thr Gly Thr Thr
    50                  55                  60

Ser Ser Thr Thr Gly Ser Thr Pro Ala Pro Thr Gly Gly Gly Gly Ser
65                  70                  75                  80

Gly Thr Gly Leu His Asp Lys Phe Lys Ala Lys Gly Lys Leu Tyr Phe
                85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr His Glu Asn Ser Leu Lys
        115                 120                 125

Trp Asp Ala Thr Glu Pro Ser Arg Asn Gln Phe Asn Phe Ala Asn Ala
    130                 135                 140

Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
            180                 185                 190

Leu Val Thr Arg Tyr Lys Gly Lys Ile Leu His Trp Asp Val Val Asn
        195                 200                 205

Glu Ile Phe Ala Glu Asp Gly Ser Leu Arg Asp Ser Val Phe Ser Arg
    210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Arg Gly Met Val Glu Lys Val Asn Lys
            260                 265                 270

Trp Ile Ala Gln Gly Ile Pro Ile Asp Gly Ile Gly Thr Gln Cys His
        275                 280                 285

Leu Ala Gly Pro Gly Gly Trp Asn Thr Ala Ala Gly Val Pro Asp Ala
    290                 295                 300

Leu Lys Ala Leu Ala Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
                325                 330                 335

Ala Cys Leu Gln Val Ser Lys Cys Val Gly Ile Thr Val Trp Gly Val
            340                 345                 350

Ser Asp Lys Asp Ser Trp Arg Ser Ser Ser Asn Pro Leu Leu Phe Asp
        355                 360                 365

Ser Asn Tyr Gln Pro Lys Ala Ala Tyr Asn Ala Leu Ile Asn Ala Leu
```

```
    370                 375                 380


<210> SEQ ID NO 5
<211> LENGTH: 2547
<212> TYPE: DNA
<213> ORGANISM: Chrysosporium lucknowense
<220> FEATURE:
<223> OTHER INFORMATION: GPD1 gene
<220> FEATURE:
<221> NAME/KEY: CDS
<222> LOCATION: (1556)..(1681)
<220> FEATURE:
<221> NAME/KEY: CDS
<222> LOCATION: (1783)..(2467)
<220> FEATURE:
<221> NAME/KEY: CDS
<222> LOCATION: (2527)..(2546)

<400> SEQUENCE: 5

tgagcagcaa tgagcagcaa tgagcattcc tgggccaccg agtctgagtg ccagtacgga      60

gtatcgtact tcgtaccggg gtttgatttg gtgacggtgc ttttcacctc tcgatgcccg     120

aaatcgggtc taagctgagt ttgatcaaat atgtgactcc aacatcgccc ccttcggcaa     180

accccgtcga cacgtgtgtc atccttccat tgcaagcgat cactcgcagg gcgtgacgat     240

gaacgagatt tttgcccgga ccgattcgcg gatatagcgg cagccgacca gccctaccac     300

actgatggcc gtgtcactag tgtatgctcc cagaaccgca agcatacact gggcaatgct     360

tggtatgcag ttgaggcagc tttatgtttc cataccettc cacttcggct cggggactcg     420

gcggggtcgc ggaagtttga cggcagccgt cgggccttag gccgagatta ccgtggttgt     480

ggcccagttt tagccgttcc cgtccgtttc ctaccggacc atgattttcg tgaaccattg     540

caatcccgaa gcgcatttcc gacgttaagg agttacctcc gctgcccaga attcatgatc     600

gtggccggct caaggcagcg tggcggggca tccgtgtcaa gctcccagga ggaggtgcgc     660

gatttcaaat ccgggccaaa acaggccaag actggctggc caaaaaaagg agcgtagacg     720

gcccgggaca tcggacgtca gctcgcagcc acccaaaacc ggtccgatct actcgcttac     780

tgtggtagtt caggtacttt tgagtagtaa aaacgctacg gcagggccgg ggggttcccc     840

ggtgacggag gtgcctctgc ggtggcgaac atcccacgca ctctcgagct acggtgacac     900

ctcgtgtcct gttggtcttg caatgctggg gcggcaggaa atgcgtcgcg ctcctcccgg     960

ccaagaccta aaacagacag cgccgcaaag tcgctcacta gcaccgcgaa acgaagatgc    1020

cccacctcaa cgcaatctgt gatgcaagca attgggaagg ctcaccccac ctcagcgagg    1080

ggctcaacca tttttattat cagctcatgc caccacaaca tgactgtttt ctttccttgc    1140

tcatcccaca tttgacaaaa atcgtcgatt aatctctttc catacaggcc gtccgcgctc    1200

tgataaccac ataaaagtct cttcagtcaa cagctcaaag ctccctcatc cctccaggta    1260

agcagccaaa gagctccccc acggaccccg cactgcctca tcccgcctgt atcggacctg    1320

cgcgacccag cagagaatcc caaacctttg ctgcttgctg cccggttccg gactgagctg    1380

caacccaagc ctttaaaaag cttttccctt ctcccacggt gtcaactctg tcctatccct    1440

ccgacatccg ttgagctcaa caactccccg aacctttac cccgcgccga gctacccctc    1500

catcaaacca ccctgacagc tcgctcactc acctccccac atcacagaaa tcaaa atg    1558
                                                             Met
                                                               1

act atc aag gtc ggc atc aac ggt ttc ggc cgt atc ggc cgt atc gtc     1606
Thr Ile Lys Val Gly Ile Asn Gly Phe Gly Arg Ile Gly Arg Ile Val
            5                  10                  15

ttc cgc aac tcc atc gag cac tcg gat gtc gag atc gtt gcc gtc aac     1654
```

```
                Phe Arg Asn Ser Ile Glu His Ser Asp Val Glu Ile Val Ala Val Asn
                     20                  25                  30

gac ccc ttc att gag ccc aag tac gct gtaagtagtt ttttttttcc                    1701
Asp Pro Phe Ile Glu Pro Lys Tyr Ala
         35                  40

ttcctcgcgt tctttcctgt tccatcgaca gtacgagatg atcttgcagg cggatcggag            1761

ctaaccgcga ttgtcgtaca g gag tac atg ctc aag tat gac tcg acc cac             1812
                        Glu Tyr Met Leu Lys Tyr Asp Ser Thr His
                                     45                  50

ggt atc ttc aac ggc acc atc gcc gtc gag ggc aac gac ctc att gtc             1860
Gly Ile Phe Asn Gly Thr Ile Ala Val Glu Gly Asn Asp Leu Ile Val
             55                  60                  65

aac ggc aag agg gtc aag ttc tac act gag cgg gmc ccc gcc aac att             1908
Asn Gly Lys Arg Val Lys Phe Tyr Thr Glu Arg Xaa Pro Ala Asn Ile
 70                  75                  80

ccc tgg arg gaa act ggt gcc gag tac atm rtc gag tcg acc ggt gtg             1956
Pro Trp Xaa Glu Thr Gly Ala Glu Tyr Ile Xaa Glu Ser Thr Gly Val
 85                  90                  95                 100

ttc acc amc acc sag aag gct agc gcc cac ctc aag ggc ggc gcc aag             2004
Phe Thr Xaa Thr Xaa Lys Ala Ser Ala His Leu Lys Gly Gly Ala Lys
                 105                 110                 115

cgc gtc atc atc tct gct ccc tcg gcc gat gcc ccc atg tac gtc atg             2052
Arg Val Ile Ile Ser Ala Pro Ser Ala Asp Ala Pro Met Tyr Val Met
             120                 125                 130

ggc gtc aac gag aag acc tac gac ggc aag gcc cag gtc atc tct aac             2100
Gly Val Asn Glu Lys Thr Tyr Asp Gly Lys Ala Gln Val Ile Ser Asn
             135                 140                 145

gcc tcg tgc acc acc aac tgc ctg gct ccc ctc gcc aag gtc atc cac             2148
Ala Ser Cys Thr Thr Asn Cys Leu Ala Pro Leu Ala Lys Val Ile His
 150                 155                 160

gac aag ttc ggc ctc gtt gag ggt ctc atg acc acc gtc cac tcc tac             2196
Asp Lys Phe Gly Leu Val Glu Gly Leu Met Thr Thr Val His Ser Tyr
165                 170                 175                 180

act gcc acc cag aag acc gtc gat ggt ccc tct gcc aag gac tgg cgt             2244
Thr Ala Thr Gln Lys Thr Val Asp Gly Pro Ser Ala Lys Asp Trp Arg
                 185                 190                 195

ggt ggc cgt ggt gct gct cag aac atc atc ccc agc agc act ggc gcc             2292
Gly Gly Arg Gly Ala Ala Gln Asn Ile Ile Pro Ser Ser Thr Gly Ala
             200                 205                 210

gcc aag gcc gtc ggc aag gtc atc cct gag ctc aac ggc aag ctc acc             2340
Ala Lys Ala Val Gly Lys Val Ile Pro Glu Leu Asn Gly Lys Leu Thr
             215                 220                 225

ggc atg tcc ctc cgt gtc ccc acc ccc aac gtt tcc gtt gtc gac ctc             2388
Gly Met Ser Leu Arg Val Pro Thr Pro Asn Val Ser Val Val Asp Leu
             230                 235                 240

acc tgc cgc ctc gag aag gag gct acc tac gac gac atc aag gcc gcc             2436
Thr Cys Arg Leu Glu Lys Glu Ala Thr Tyr Asp Asp Ile Lys Ala Ala
245                 250                 255                 260

atc aag gag gcc gcc gcc ggc ccc ctc aag g gtgagttatc tggttccttt             2487
Ile Lys Glu Ala Ala Ala Gly Pro Leu Lys
                 265                 270

ttttttttt ggagaacgac acatgctgat aaaacccag gc atc ctc gac tac act            2543
                                            Gly Ile Leu Asp Tyr Thr
                                                             275

gag g                                                                        2547
Glu

<210> SEQ ID NO 6
<211> LENGTH: 277
<212> TYPE: PRT
```

<213> ORGANISM: Chrysosporium lucknowense
<220> FEATURE:
<221> NAME/KEY: MOD_RES
<222> LOCATION: (80)
<223> OTHER INFORMATION: Asp or Ala
<220> FEATURE:
<221> NAME/KEY: MOD_RES
<222> LOCATION: (86)
<223> OTHER INFORMATION: Lys or Arg
<220> FEATURE:
<221> NAME/KEY: MOD_RES
<222> LOCATION: (95)
<223> OTHER INFORMATION: Ile or Val
<220> FEATURE:
<221> NAME/KEY: MOD_RES
<222> LOCATION: (103)
<223> OTHER INFORMATION: Asn or Thr
<220> FEATURE:
<221> NAME/KEY: MOD_RES
<222> LOCATION: (105)
<223> OTHER INFORMATION: Gln or Glu

<400> SEQUENCE: 6

```
Met Thr Ile Lys Val Gly Ile Asn Gly Phe Gly Arg Ile Gly Arg Ile
  1               5                  10                  15

Val Phe Arg Asn Ser Ile Glu His Ser Asp Val Glu Ile Val Ala Val
             20                  25                  30

Asn Asp Pro Phe Ile Glu Pro Lys Tyr Ala Glu Tyr Met Leu Lys Tyr
         35                  40                  45

Asp Ser Thr His Gly Ile Phe Asn Gly Thr Ile Ala Val Glu Gly Asn
     50                  55                  60

Asp Leu Ile Val Asn Gly Lys Arg Val Lys Phe Tyr Thr Glu Arg Xaa
 65                  70                  75                  80

Pro Ala Asn Ile Pro Trp Xaa Glu Thr Gly Ala Glu Tyr Ile Xaa Glu
                 85                  90                  95

Ser Thr Gly Val Phe Thr Xaa Thr Xaa Lys Ala Ser Ala His Leu Lys
            100                 105                 110

Gly Gly Ala Lys Arg Val Ile Ile Ser Ala Pro Ser Ala Asp Ala Pro
        115                 120                 125

Met Tyr Val Met Gly Val Asn Glu Lys Thr Tyr Asp Gly Lys Ala Gln
    130                 135                 140

Val Ile Ser Asn Ala Ser Cys Thr Thr Asn Cys Leu Ala Pro Leu Ala
145                 150                 155                 160

Lys Val Ile His Asp Lys Phe Gly Leu Val Glu Gly Leu Met Thr Thr
                165                 170                 175

Val His Ser Tyr Thr Ala Thr Gln Lys Thr Val Asp Gly Pro Ser Ala
            180                 185                 190

Lys Asp Trp Arg Gly Gly Arg Gly Ala Ala Gln Asn Ile Ile Pro Ser
        195                 200                 205

Ser Thr Gly Ala Ala Lys Ala Val Gly Lys Val Ile Pro Glu Leu Asn
    210                 215                 220

Gly Lys Leu Thr Gly Met Ser Leu Arg Val Pro Thr Pro Asn Val Ser
225                 230                 235                 240

Val Val Asp Leu Thr Cys Arg Leu Glu Lys Glu Ala Thr Tyr Asp Asp
                245                 250                 255

Ile Lys Ala Ala Ile Lys Glu Ala Ala Ala Gly Pro Leu Lys Gly Ile
            260                 265                 270

Leu Asp Tyr Thr Glu
        275
```

<210> SEQ ID NO 7

<211> LENGTH: 32
<212> TYPE: PRT
<213> ORGANISM: Artificial Sequence
<220> FEATURE:
<223> OTHER INFORMATION: Description of Artificial Sequence: Synthetic
consensus sequence
<220> FEATURE:
<221> NAME/KEY: MOD_RES
<222> LOCATION: (1)
<223> OTHER INFORMATION: Trp or Tyr
<220> FEATURE:
<221> NAME/KEY: MOD_RES
<222> LOCATION: (2)
<223> OTHER INFORMATION: Gly or Ala
<220> FEATURE:
<221> NAME/KEY: MOD_RES
<222> LOCATION: (7)
<223> OTHER INFORMATION: Gln, Ile or Asn
<220> FEATURE:
<221> NAME/KEY: MOD_RES
<222> LOCATION: (8)
<223> OTHER INFORMATION: Gln or Asn
<220> FEATURE:
<221> NAME/KEY: MOD_RES
<222> LOCATION: (9)
<223> OTHER INFORMATION: Trp, Phe or Tyr
<220> FEATURE:
<221> NAME/KEY: MOD_RES
<222> LOCATION: (10)
<223> OTHER INFORMATION: Ser, Thr, Asn or Gln
<220> FEATURE:
<221> NAME/KEY: MOD_RES
<222> LOCATION: (12)
<223> OTHER INFORMATION: Phe, Ala or Cys
<220> FEATURE:
<221> NAME/KEY: MOD_RES
<222> LOCATION: (13)
<223> OTHER INFORMATION: Thr, Arg or Lys
<220> FEATURE:
<221> NAME/KEY: MOD_RES
<222> LOCATION: (14)
<223> OTHER INFORMATION: Thr, Cys or Asn
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (18)
<223> OTHER INFORMATION: Gly or Pro
<220> FEATURE:
<221> NAME/KEY: MOD_RES
<222> LOCATION: (19)
<223> OTHER INFORMATION: Ser, Thr, Phe, Leu, Ala or not present
<220> FEATURE:
<221> NAME/KEY: MOD_RES
<222> LOCATION: (20)
<223> OTHER INFORMATION: Thr or Lys
<220> FEATURE:
<221> NAME/KEY: MOD_RES
<222> LOCATION: (22)
<223> OTHER INFORMATION: Val, Thr, Arg, Glu or Lys
<220> FEATURE:
<221> NAME/KEY: MOD_RES
<222> LOCATION: (23)
<223> OTHER INFORMATION: Lys, Gln or Ala
<220> FEATURE:
<221> NAME/KEY: MOD_RES
<222> LOCATION: (24)
<223> OTHER INFORMATION: Gln or Ile
<220> FEATURE:
<221> NAME/KEY: MOD_RES
<222> LOCATION: (26)
<223> OTHER INFORMATION: Gln, Asp or Ala
<220> FEATURE:
<221> NAME/KEY: MOD_RES
<222> LOCATION: (27)
<223> OTHER INFORMATION: Trp, Phe or Tyr
<220> FEATURE:
<221> NAME/KEY: MOD_RES

```
<222> LOCATION: (29)
<223> OTHER INFORMATION: Tyr, Ser, His or Ala
<220> FEATURE:
<221> NAME/KEY: MOD_RES
<222> LOCATION: (32)
<223> OTHER INFORMATION: Leu, Ile, Gln, Val or Thr

<400> SEQUENCE: 7

Xaa Xaa Gln Cys Gly Gly Xaa Xaa Xaa Xaa Gly Xaa Xaa Xaa Cys Xaa
  1               5                  10                  15

Xaa Xaa Xaa Xaa Cys Xaa Xaa Xaa Asn Xaa Xaa Tyr Xaa Gln Cys Xaa
             20                  25                  30


<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Ser Gly Glu Arg Lys
  1               5


<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide sequence

<400> SEQUENCE: 9

Val Cys Gln Phe
  1


<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (3)
<223> OTHER INFORMATION: Any amino acid or preferably Val, Thr, Arg,
      Glu, Gln or Lys or most preferably Gln or Glu

<400> SEQUENCE: 10

Val Cys Xaa Phe Val
  1               5


<210> SEQ ID NO 11
<211> LENGTH: 4
<212> TYPE: PRT
<213> ORGANISM: Artificial
<220> FEATURE:
<223> OTHER INFORMATION: Description of Artificial Sequence: Synthetic
      consensus sequence
<220> FEATURE:
<221> NAME/KEY: misc
<222> LOCATION: (2)..(2)
<223> OTHER INFORMATION: Xaa is any amino acid or preferably Val, Thr,
      Arg, Glu, Gln, or Lys, or most preferably Gln or Glu.

<400> SEQUENCE: 11

Cys Xaa Phe Val
1
```

-continued

```
<210> SEQ ID NO 12
<211> LENGTH: 4
<212> TYPE: PRT
<213> ORGANISM: Artificial
<220> FEATURE:
<223> OTHER INFORMATION: Description of Artificial Sequence: Synthetic
      consensus sequence
<220> FEATURE:
<221> NAME/KEY: misc
<222> LOCATION: (3)..(3)
<223> OTHER INFORMATION: Xaa is any amino acid or preferably Val, Thr,
      Arg, Glu, Gln, or Lys, or most preferably Gln or Glu.

<400> SEQUENCE: 12

Val Cys Xaa Phe
1
```

EXPRESSION-REGULATING SEQUENCES AND EXPRESSION PRODUCTS IN THE FIELD OF FILAMENTOUS FUNGI

The present application is the national phase application under 35 U.S.C. §371 of International Application No. PCT/NL01/00301, filed on Apr. 17, 2001, which claims the benefit of European Patent Application No. 00201343.1, filed on Apr. 13, 2000, and is a continuation-in-part of U.S. Ser. No. 09/548,938, filed Apr. 13, 2000, now U.S. Pat. No. 6,573,086, which is a continuation-in-part of International Application No. PCT/NL99/00618, filed on Oct. 6, 1999, which is a continuation-in-part of International Patent Application No. PCT/EP98/06496, filed Oct. 6, 1998.

FIELD OF THE INVENTION

The subject invention relates to novel enzymes derived from filamentous fungi, especially from strains of the genus *Chrysosporium*, and to coding sequences and expression-regulating sequences for these enzymes.

BACKGROUND TO THE INVENTION

A number of hosts for gene expression and methods of transformation have been disclosed in the prior art. Bacteria are often mentioned e.g. *Escherichia coli*. *E. coli* is however a micro-organism incapable of secretion of a number of proteins or polypeptides and as such is undesirable as host cell for production of protein or polypeptide at the industrial level. An additional disadvantage for *E. coli*, which is valid also for bacteria in general, is that prokaryotes cannot provide additional modifications required for numerous eukaryotic proteins or polypeptides to be produced in an active form. Glycosylation of proteins and proper folding of proteins are examples of processing required to ensure an active protein or polypeptide is produced. To ensure such processing one can sometimes use mammalian cells; however, the disadvantage of such cells is that they are often difficult to maintain and require expensive media. Such transformation systems are therefore not practical for production of proteins or polypeptides at the industrial level. They may be cost efficient for highly priced pharmaceutical compounds requiring relatively low amounts, but certainly not for industrial enzymes.

A number of fungal expression systems have been developed e.g. *Aspergillus niger, Aspergillus awamori, Aspergillus nidulans, Trichoderma reesei*. A number of others have been suggested but for various reasons have not found wide-spread acceptance or use. In general terms the ideal host must fulfil a large number of criteria:

- The ideal host must be readily fermented using inexpensive medium.
- The ideal host should use the medium efficiently.
- The ideal host must produce the polypeptide or protein in high yield, i.e. must exhibit high protein to biomass ratio.
- The ideal host should be capable of efficient secretion of the protein or polypeptide.
- The ideal host must enable ease of isolation and purification of the desired protein or poly-peptide.
- The ideal host must process the desired protein or polypeptide such that it is produced in an active form not requiring additional activation or modification steps.
- The ideal host should be readily transformed.
- The ideal host should allow a wide range of expression regulatory elements to be used thus ensuring ease of application and versatility.
- The ideal host should allow use of easily selectable markers that are cheap to use.
- The ideal host should produce stable transformants.
- The ideal host should allow cultivation under conditions not detrimental to the protein or polypeptide product, e.g. low viscosity, low shear.

WO 96/02563 and U.S. Pat. Nos. 5,602,004, 5,604,129 and 5,695,985 to Novo Nordisk describe the drawbacks of *Aspergillus* and *Trichoderma* systems and suggest that cultivation conditions for other fungi may be more suited to large scale protein production. The only examples provided for any transformed cultures are those of *Myceliophthora thermophila, Acremonium alabamense, Thielavia terrestris* and *Sporotrichum cellulophilum* strains. The *Sporotrichum* strain is reported to lyse and produce green pigment under fermentation conditions not leading to such results for the other strains. A non-sporulating mutant of *Thielavia terrestris* is described as being the organism of choice by virtue of its morphology. However it is also stated that the protoplasting efficiency of *Thielavia* and *Acremonium* (whereby the *Acremonium* strain used was the imperfect state of the *Thielavia* strain used) is low and that hygromycin was not useful as a selection marker. A large number of others are suggested as being potentially useful by virtue of their morphology but no transformation thereof is described. The suggested strains are *Corynascus, Thermoascus, Chaetomium, Ctenomyces, Scytalidium* and *Talaromyces*. The transformed hosts are mentioned as only producing low levels of the introduced *Humicola xylanase* with *Thielavia* producing the lowest amount; however, the information is ambiguous and could actually infer *Thielavia* was the best embodiment. The nomenclature of this reference is based on the ATCC names of Industrial Fungi of 1994. Thus it is apparent that no high degree of heterologous expression was achieved and in fact no positive correlation could be derived between the postulated morphology and the degree of expression. If any correlation could be made, it was more likely to be negative. According to the 1996 ATCC fungal classification *Sporotrichum thermophilum* ATCC 20493 is a *Myceliophthora thermophila* strain. Currently the strain is still identified as *Myceliophthora thermophila*. The unpredictability of the art is apparent from these recent disclosures.

WO 97/26330 of Novo Nordisk suggests a method of obtaining mutants of filamentous fungal parent cells having an improved property for production of heterologous polypeptide. The method comprises first finding a specific altered morphology followed by assessing whether a transformant produces more heterologous polypeptide than the parent. The method is illustrated only for strains of *Fusarium* A3/5 and *Aspergillus oryzae*. The method is suggested to be applicable for *Aspergillus, Trichoderma, Thielavia, Fusarium, Neurospora, Acremonium, Tolyplocadium, Humicola, Scytalidium, Myceliophthora* or *Mucor*. As stated above, the unpredictability in the art and also the unpredictability of the method of the cited application do not provide a generally applicable teaching with a reasonable expectation of success.

In WO 00/20555, we have described an alternative fungal expression system with the simplicity of use of the above-mentioned *Aspergilli* and *Trichoderma* fulfilling the above requirements. The new system provides the additional advantages that transformation rates are higher than those for the frequently used *Trichoderma reesei* system. In addition the culture conditions offer the additional bonus of being advantageous for the polypeptide product.

DETAILED DESCRIPTION OF THE INVENTION

We now describe a number of industrially interesting enzymes derived from *Chrysosporium* strains, together with full sequence information. We also describe novel promoter systems derived from *Chrysosporium* strains and useful for expressing homologous and heterologous genes.

The present invention is in particular concerned with glycosyl hydrolases of the families 7 (e.g. cellobiohydrolases) and 10 (e.g. xylanases), and glyceraldehyde phosphate dehydrogenases, as identified by their amino acid sequence, as well as peptides derived from these enzymatic proteins, and with nucleic acid sequences encoding these peptides and proteins, as well as, in particular, with regulating sequences related to these genes.

In particular, the present invention pertains to isolated or recombinant enzymic proteins or active parts thereof of the three classes referred to above, including mutants thereof having at least a certain degree of sequence identity as specified in the further disclosure and in the claims, as well as nucleic acid sequences encoding these proteins or parts thereof, and/or nucleic acid sequences regulating their expression. These enzymes are especially: (1) a glycosyl hydrolase of family 7 (cellobiohydrolase, CBH1) having at least 75%, preferably at least 80% or even at least 85% amino acid identity with the sequence of SEQ ID No 2; (2) a glycosyl hydrolase of family 10 (endo-xylanase XYL1) having at least 70%, preferably at least 75% or even at least 80% amino acid identity with the sequence of SEQ ID No 4; and (3) a glyceraldehyde phosphate dehydrogenase (GPD1) having at least 86%, preferably at least 90% or even at least1 93% amino acid identity with the sequence of SEQ ID No 6. Polypeptides and nucleic acid sequences encoding these polypeptides, having at least 20, preferably at least 30 contiguous amino acids of SEQ ID No's 2, 4 and 6 are also a preferred part of the invention. The corresponding nucleotide sequences are depicted in SEQ ID No's 1 (cbh1), 3 (xyl1) and 5 (gpd1), respectively.

The recombinant enzymes may comprise essentially the complete protein, or a truncated protein having at least part of the enzymatic activity. Such truncated part may be the catalytic domain, or at least about 75% of the amino acids thereof. By way of example, the catalytic domain of the CBH1 according to the invention comprises the amino acids 20-495 of the aminoacid sequence of SEQ ID No. 2, and the catalytic domain of the XYL1 according to the invention comprises the aminoacids 54-384 of the aminoacid sequence of SEQ ID No. 4. The catalytic domain may or may not be combined with a signal sequence originating from another protein and/or with a carbohydrate-binding domain from another enzymic protein. Alternatively, the cellulose-binding domain of the enzymes of the invention (CBH1 and XYL1) may be fused to catalytic domains of other enzymic proteins.

The nucleic acid sequences according to the invention may be complete protein-encoding regions or oligonucleotides or, preferentially, expression-regulating sequences. Oligonucleotides may be used also as probes for identifying genes corresponding to, but not identical to the genes of SEQ ID No.'s 1, 3 and 5; these genes, when fulfilling the percentage identity criteria defined herein, as well as encoding and non-encoding parts thereof and their expression products are also part of the invention. Oligonucleotides are preferably 15-75, most preferably 20-50 nucleotides in length.

The invention also pertains to expression systems (cassettes) comprising either an expression-regulating region (including a promoter) of any of the three protein classes fused to a gene encoding another protein of interest, or an encoding region of any of these proteins fused to another expression regulating region, or both the expression-regulating region and the protein-encoding region of these novel proteins. The expression-regulating region comprises at least 60%, preferably at least 70%, more preferably at least 75% or even 80% of the 5'-non-coding region of SEQ ID No.'s 1, 3 and 5, and/or at least 20, especially at least 40 contiguous nucleotides from these 5' non-coding regions. Terminating sequences similarly derived from the 3' non-coding regions of the genes of the invention are also useful in expressing cassettes, whether combined with homologous or heterologous genes.

The polynucleotides and oligonucleotides of the invention can have the minimum sequence identity with the corresponding sequences of SEQ ID NO's 1, 3 or 5, or, alternatively hybridise under stringent conditions with these given sequences. Stringent hybridisation conditions are those as understood in the art, e.g. hybridisation in 6×SSC (20×SSC per 1000 ml: 175.3 g NaCl, 107.1 g sodium citrate. $5H_2O$, pH 7.0), 0.1% SDS, 0.05% sodium pyrophosphate, 5*Denhardt's solution and 20 μg/ml denatured herring sperm DNA at 56° C. for 18-24 hrs followed by two 30 min. washes in 5×SSC, 0.1% SDS at 56° C. and two 30 min. washes in 2×SSC, 0.1% SSC at 56° C.

These expression systems may be contained in a *Chrysosporium* host, such as a *Chrysosporium lucknowense* host, or in another non-fungal or, preferably, fungal host. Examples of other fungal hosts are other *Chrysosporium* species or strains, *Fusarium* species, *Aspergillus* species etc. Such host may be advantageously a host that does not itself, intrinsically or as a result of the culture conditions, produce a protein corresponding to the protein of interest, so as to simplify the recovery of the protein of interest.

Where reference is made in this specification and in the appending claims to "polypeptides" or "peptides" or "polypeptides of interest" or "peptides of interest" as the products of the expression system of the invention, this term also comprise proteins, i.e. polypeptides having a particular function and/or secondary and/or tertiary structure. Where reference is made to a percentage amino acid identity, such identity relates to a complete protein or to a specific part defined by initial and final amino acid number, as determined by the conventionally used BLAST algorithm.

In the fungal expression system described in WO 00/20555, the pH of the culture medium can be neutral or alkaline thus no longer subjecting the produced protein or polypeptide to aggressive and potentially inactivating acid pH. It is also possible to culture at acid pH such as pH 4 for cases where the protein or polypeptide is better suited to an acidic environment. Suitably culture can occur at a pH between 4.0-10.0. A preference however exists for neutral to alkaline pH as the host strain exhibits better growth at such pH, e.g. between 6 and 9. Growth at alkaline pH which can be from pH 8 up and can even be as high as 10 is also a good alternative for some cases. Also the cultivation temperature of such host strains is advantageous to the stability of some types of produced polypeptide. The cultivation temperature is suitably at a temperature of 23-43° C. Clearly such conditions are of particular interest for production of mammalian polypeptides. The selected temperature will depend on cost effectiveness of the cultivation and sensitivity of the polypeptide or cultivation strain.

It has also been ascertained that the biomass to viscosity relation and the amount of protein produced is exceedingly favourable for the *Chrysosporium* host. Comparisons have been carried out with *Trichoderma longibrachiatum* (formerly also known as *Trichoderma reesei*) and with *Aspergillus niger*. *Trichoderma longibrachiatum* gave 2.5-5 g/l biomass, *Aspergillus niger* gave 5-10 g/l biomass and the *Chrysosporium* host gave 0.5-1 g/l biomass under their respective optimised conditions. This thus offers 5-10 fold improvement over the commercially used strains. The subject invention is directed at expression systems comprising a nucleic acid sequence encoding a heterologous protein or polypeptide, said nucleic acid sequence being operably linked to an expression regulating region described below and optionally a secretion signal encoding sequence and/or a carrier protein encoding sequence. Preferably a recombinant strain according to the invention will secrete the polypeptide of interest. This will avoid the necessity of disrupting the cell in order to isolate the polypeptide of interest and also minimise the risk of degradation of the expressed product by other components of the host cell.

*Chrysosporium* can be defined by morphology consistent with that disclosed in Barnett and Hunter 1972, Illustrated Genera of Imperfect Fungi, 3rd Edition of Burgess Publishing Company. Other sources providing details concerning classification of fungi of the genus *Chrysosporium* are known e.g. Sutton Classification (Van Oorschot, C. A. N. (1980) "A revision of *Chrysosporium* and allied genera" in Studies in Mycology No. 20 of the CBS in Baarn, The Netherlands p1-36). CBS is one of the depository institutes of the Budapest Treaty. According to these teachings the genus *Chrysosporium* falls within the family Moniliaceae which belongs to the order Hyphomycetales. The following strains are defined as *Chrysosporium* but the definition of *Chrysosporium* is not limited to these strains: *C. botryoides, C. carmichaelii, C. crassitunicatum, C. europae, C. evolceannui, C. farinicola, C. fastidium, C. filiforme, C. georgiae, C. globiferum, C. globiferum* var. *articulatum, C. globiferum* var. *niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. pseudomerdarium, C. pyriformis, C. queenslandicum, C. sigleri, C. sulfureum, C. synchronum, C. tropicum, C. undulatum, C. vallenarense, C. vespertilium, C. zonalum.*

*C. lucknowense* forms one of the species of *Chrysosporium* that have raised particular interest as it has provided a natural high producer of cellulase proteins (WO 98/15633 and related U.S. Pat. No. 5,811,381). The characteristics of this *Chrysosporium lucknowense* are:

Colonies attain 55 mm diameter on Sabouraud glucose agar in 14 days, are cream-coloured, felty and fluffy; dense and 3-5 mm high; margins are defined, regular, and fimbriate; reverse pale yellow to cream-coloured. Hyphae are hyaline, smooth- and thin-walled, little branched. Aerial hyphae are mostly fertile and closely septate, about 1-3.5 μm wide. Submerged hyphae are infertile, about 1-4.5 μm wide, with the thinner hyphae often being contorted. Conidia are terminal and lateral, mostly sessile or on short, frequently conical protrusions or short side branches. Conidia are solitary but in close proximity to one another, 1-4 conidia developing on one hyphal cell, subhyaline, fairly thin- and smooth-walled, mostly subglobose, also clavate orobovoid, 1-celled, 2.5-11×1.5-6 μm, with broad basal scars (1-2 μm). Intercalary conidia are absent. Chlamydospores are absent. ATCC 44006, CBS 251.72, CBS 143.77 and CBS 272.77 are examples of *Chrysosporium lucknowense* strains and other examples are provided in WO 98/15633 (U.S. Pat. No. 5,811,381).

A further strain was isolated from this species with an even higher production capacity for cellulases. This strain is called C1 by its internal notation and was deposited with the International Depository of the All Russian Collection of microorganisms of the Russian Academy of Sciences Bakrushina Street 8, Moscow, Russia 113184 on Aug. 29, 1996, as a deposit according to the Budapest Treaty and was assigned Accession Number VKM F-3500D. It is called *Chrysosporium lucknowense* Garg 27K. The characteristics of the C1 strain are as follows:

Colonies grow to about 55-66 mm diameter in size on potato-dextrose agar in about 7 days; are white-cream-coloured, felty, 2-3 μm high at the centre; margins are defined, regular, fimbriate; reverse pale, cream-coloured. Hyphae are hyaline, smooth- and thin-walled, little branched. Aerial hyphae are fertile, septate, 2-3 mm wide. Submerged hyphae are infertile. Conidia are terminal and lateral; sessile or on short side branches; absent; solitary, but in close proximity to one another, hyaline, thin- and smooth-walled, subglobose, clavate or obovoid, 1-celled, 4-10 μm. Chlamydospores are absent. Intercalary conidia are absent.

The method of isolation of the C1 strain is described in WO 98/15633, U.S. Pat. No. 5,811,381, and U.S. Pat. No. 6,015,707. Also included within the definition of *Chrysosporium* are strains derived from *Chrysosporium* predecessors including those that have mutated somewhat either naturally or by induced mutagenesis. Mutants of *Chrysosporium* can be obtained by induced mutagenesis, especially by a combination of irradiation and chemical mutagenesis.

For example strain C1 was mutagenised by subjecting it to ultraviolet light to generate strain UV13-6. This strain was subsequently further mutated with N-methyl-N'-nitro-N-nitrosoguanidine to generate strain NG7C-19. The latter strain in turn was subjected to mutation by ultraviolet light resulting in strain UV18-25. During this mutation process the morphological characteristics have varied somewhat in culture in liquid or on plates as well as under the microscope. With each successive mutagenesis the cultures showed less of the fluffy and felty appearance on plates that are described as being characteristic of *Chrysosporium*, until the colonies attained a flat and matted appearance. A brown pigment observed with the wild type strain in some media was also less prevalent in mutant strains. In liquid culture the mutant UV18-25 was noticeably less viscous than the wild type strain C1 and the mutants UV13-6 and NG7C-19. While all strains maintained the gross microscopic characteristics of *Chrysosporium*, the mycelia became narrower with each successive mutation and with UV18-25 distinct fragmentation of the mycelia could be observed. This mycelial fragmentation is likely to be the cause of the lower viscosity associated with cultures of UV18-25. The ability of the strains to sporulate decreased with each mutagenic step. The above illustrates that for a strain to belong to the genus *Chrysosporium* there is some leeway from the above morphological definition. At each mutation step production of cellulase and extracellular proteins has in addition also increased, while several mutations resulted in decrease of protease expression. Criteria with which fungal taxonomy can be determined are available from CBS, VKMF and ATCC for example. The strains internally designated as *Chrysosporium* strain C1, strain UV13-6, strain NG7C-19 and strain UV18-25, have been deposited in accordance with the Budapest Treaty with the All Russian Collection (VKM) depository institute in Moscow. Wild type C1 strain was deposited with number VKM F-3500 D, deposit date 29-08-1996, C1 UV13-6 mutant was deposited as VKM F-3632 D (02-09-1998), C1 NG7c-19 mutant was deposited as VKM F-3633 D (02-09-1998) and C1 UV18-25 mutant was deposited as VKM F-3631 D (02-09-1998).

It is preferable to use non-toxic *Chrysosporium* strains of which a number are known in the art as this will reduce risks to the environment upon large scale production and simplify production procedures with the concomitant reduction in costs.

An expression-regulating region is a DNA sequence recognised by the host *Chrysosporium* strain for expression. It comprises a promoter sequence operably linked to a nucleic acid sequence encoding the polypeptide to be expressed. The promoter is linked such that the positioning vis-à-vis the initiation codon of the sequence to be expressed allows expression. The promoter sequence can be constitutive or inducible. Any expression regulating sequence or combination thereof capable of permitting expression of a polypeptide from a *Chrysosporium* strain is envisaged. The expression regulating sequence is suitably a fungal expression-regulating region e.g. an ascomycete regulating region. Suitably the fungal expression regulating region is a regulating region from any of the following genera of fungi: *Aspergillus, Trichoderma, Chrysosporium, Hansenula, Mucor, Pichia, Neurospora, Tolypocladium, Rhizomucor, Fusarium, Penicillium, Saccharomyces, Talaromyces* or alternative sexual forms thereof like *Emericella, Hypocrea* e.g. the cellobiohydrolase promoter from *Trichoderma*, glucoamylase promoter from *Aspergillus*, glyceraldehyde phosphate dehydrogenase promoter from *Aspergillus*, alcohol dehydrogenase A and alcohol dehydrogenase R promoter of *Aspergillus*, TAKA amylase promoter from *Aspergillus*, phosphoglycerate and cross-pathway control promoters of *Neurospora*, aspartic proteinase promoter of *Rhizomucor miehei*, lipase promoter of *Rhizomucor miehei* and beta-galactosidase promoter of *Penicillium canescens*. An expression regulating sequence from the same genus as the host strain is extremely suitable, as it is most likely to be specifically adapted to the specific host. Thus preferably the expression regulating sequence is one from a *Chrysosporium* strain.

Preferably an expression-regulating region enabling high expression in the selected host is applied. This is preferably an expression-regulating region derived from *Chrysosporium* according to the invention. It can also be a high expression-regulating region derived from a heterologous host, such as are well known in the art. Specific examples of proteins known to be expressed in large quantities and thus providing suitable expression regulating sequences for the invention are without being limited thereto hydrophobin, protease, amylase, xylanase, pectinase, esterase, beta-galactosidase, cellulase (e.g. endo-glucanase, cellobiohydrolase) and polygalacturonase. The high production has been ascertained in both solid state and submerged fermentation conditions. Assays for assessing the presence or production of such proteins are well known in the art. The catalogues of Sigma and Megazyme for example provide numerous examples. Megazyme is located at Bray Business Park, Bray, County Wicklow in Ireland. Sigma Aldrich has many affiliates world wide e.g. USA P.O. Box 14508 St. Louis Mo. For cellulase we refer to commercially available assays such as CMCase assays, endoviscometric assays, Avicelase assays, beta-glucanase assays, RBBCMCase assays, Cellazyme C assays. Xylanase assays are also commercially available (e.g. DNS and Megazyme). Alternatives are well known to a person skilled in the art and can be found from general literature concerning the subject and such information is considered incorporated herein by reference. By way of example we refer to "Methods in Enzymology" Volume 1, 1955 right through to volumes 297-299 of 1998. Suitably a *Chrysosporium* promoter sequence is applied to ensure good recognition thereof by the host.

We have found that heterologous expression-regulating sequences work as efficiently in *Chrysosporium* as native *Chrysosporium* sequences. This allows well known constructs and vectors to be used in transformation of *Chrysosporium* as well as offering numerous other possibilities for constructing vectors enabling good rates of expression in this novel expression and secretion host. For example standard Aspergillus transformation techniques can be used as described for example by Christiansen et al in Bio/Technol. 6:1419-1422 (1988). Other documents providing details of *Aspergillus* transformation vectors, e.g. U.S. Pat. Nos. 4,816,405, 5,198,345, 5,503,991, 5,364,770 and 5,578,463, EP-B-215.594 (also for *Trichoderma*) and their contents are incorporated by reference. As extremely high expression rates for cellulase have been ascertained for *Chrysosporium* strains, the expression regulating regions of such proteins are particularly preferred. We refer for specific examples to the previously mentioned deposited *Chrysosporium* strains.

A nucleic acid construct comprising a nucleic acid expression regulatory region from *Chrysosporium*, preferably from *Chrysosporium lucknowense* or a derivative thereof forms a preferred embodiment of the invention, as does the mutant *Chrysosporium* strain comprising such operably linked to a gene encoding a polypeptide to be expressed. Such a nucleic acid construct will be an expression regulatory region from *Chrysosporium* associated with cellulase or xylanase expression, preferably cellobiohydrolase expression, or glyceraldehyde phosphate dehydrogenase expression, as detailed below. The nucleic acid sequence according to the invention can suitably be obtained from a *Chrysosporium* strain, such strain being defined elsewhere in the description. The manner in which promoter sequences can be determined are numerous and well known in the art. Nuclease deletion experiments of the region upstream of the ATG codon at the beginning of the relevant gene will provide such sequence. Also for example analysis of consensus sequences can lead to finding a gene of interest. Using hybridisation and amplification techniques one skilled in the art can readily arrive at the corresponding promoter sequences.

The promoter sequences of C1 endoglucanases were identified in this manner, by cloning the corresponding genes. Preferred promoters according to the invention are the 55 kDa cellobiohydrolase (CBH1) promoter, the 30 kDa xylanase (Xyl1) promoters, and the glyceraldehyde phosphate dehydrogenase promoter, as the enzymes are expressed at high level by their own promoters. The corresponding promoter sequences are identified in a straightforward manner by cloning as described in WO 00/20555, using the sequence information given in SEQ ID No. 1 (for CBH1) and SEQ ID No. 3 (for Xyl1), respectively. The promoters of the carbohydrate-degrading enzymes of *Chrysosporium*, especially C1 promoters, can advantageously be used for expressing desired polypeptides in a host organism, especially a fungal or other microbial host organism. Promoter sequences having at least 65%, preferably at least 70%, most preferably at least 75% nucleotide sequence identity with the sequence given in SEQ ID No's 1, 3 and 5, or with the sequences found for other *Chrysosporium* genes, are part of the present invention.

For particular embodiments of the recombinant strain and the nucleic acid sequence according to the invention we also refer to the examples. We also refer for the recombinant strains to prior art describing high expression promoter sequences in particular those providing high expression in fungi e.g. such as are disclosed for *Aspergillus* and *Trichoderma*. The prior art provides a number of expression regulating regions for use in Aspergillus e.g. U.S. Pat. No. 5,252,726 of Novo and U.S. Pat. No. 5,705,358 of Unilever. The contents of such prior art are hereby incorporated by reference.

The hydrophobin gene is a fungal gene that is highly expressed. It is thus suggested that the promoter sequence of a hydrophobin gene, preferably from *Chrysosporium*, may be suitably applied as expression regulating sequence in a suitable embodiment of the invention. *Trichoderma reesei* and *Trichoderma harzianum* gene sequences for hydrophobin have been disclosed for example in the prior art as well as a gene sequence for *Aspergillus fumigatus* and *Aspergillus nidulans* and the relevant sequence information is hereby incorporated by reference (Munoz et al, *Curr. Genet.* 1997, 32(3):225-230; Nakari-Setala T. et al, *Eur. J. Biochem.* 1996 15:235 (1-2):248-255, M. Parta et al, *Infect. Immun.* 1994 62 (10): 4389-4395 and Stringer M. A. et al. *Mol. Microbiol.* 1995 16(1):33-44). Using this sequence information a person skilled in the art can obtain the expression regulating sequences of *Chrysosporium* hydrophobin genes without undue experimentation following standard techniques as suggested already above. A recombinant *Chrysosporium* strain according to the invention can comprise a hydrophobin-regulating region operably linked to the sequence encoding the polypeptide of interest.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. Filamentous fungal promoters in which creA sites are present have been described. Such creA sites can be mutated to ensure the glucose repression normally resulting from the presence of the non-mutated sites is eliminated. Gist-Brocades' WO 94/13820 illustrates this principle. Use of such a promoter enables production of the polypeptide encoded by the nucleic acid sequence regulated by the promoter in the presence of glucose. The same principle is also apparent from WO 97/09438. These promoters can be used either with or without their creA sites. Mutants in which the creA sites have been mutated can be used as expression regulating sequences in a recombinant strain according to the invention and the nucleic acid sequence it regulates can then be expressed in the presence of glucose. Such *Chrysosporium* promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the protein or polypeptide in the presence of glucose.

Terminator sequences are also expression-regulating sequences and these are operably linked to the 3' terminus of the sequence to be expressed. Any fungal terminator is likely to be functional in the host *Chrysosporium* strain according to the invention. Examples are *A. nidulans* trpC terminator (1), *A. niger* alpha-glucosidase terminator (2), *A. niger* glucoamylase terminator (3), *Mucor miehei* carboxyl protease terminator (U.S. Pat. No. 5,578,463) and the *Trichoderma reesei* cellobiohydrolase terminator. Naturally *Chrysosporium* terminator sequences will function in *Chrysosporium* and are suitable e.g. CBH1 terminator.

A suitable recombinant *Chrysosporium* strain to be used according to the invention has the nucleic acid sequence to be expressed operably linked to a sequence encoding the amino acid sequence defined as signal sequence. A signal sequence is an amino acid sequence which when operably linked to the amino acid sequence of the expressed polypeptide allows secretion thereof from the host fungus. Such a signal sequence may be one normally associated with the heterologous polypeptide or may be one native to the host. It can also be foreign to both host and the polypeptide. The nucleic acid sequence encoding the signal sequence must be positioned in frame to permit translation of the signal sequence and the heterologous polypeptide. Any signal sequence capable of permitting secretion of a polypeptide from a *Chrysosporium* strain is envisaged. Such a signal sequence is suitably a fungal signal sequence, preferably an ascomycete signal sequence.

Suitable examples of signal sequences can be derived from yeasts in general or any of the following specific genera of fungi: *Aspergillus, Trichoderma, Chrysosporium, Pichia, Neurospora, Rhizomucor, Hansenula, Humicola, Mucor, Tolypocladium, Fusarium, Penicillium, Saccharomyces, Talaromyces* or alternative sexual forms thereof like *Emericella, Hypocrea*. Signal sequences that are particularly useful are often natively associated with the following proteins a cellobiohydrolase, an endoglucanase, a beta-galactosidase, a xylanase, a pectinase, an esterase, a hydrophobin, a protease or an amylase. Examples include amylase or glucoamylase of *Aspergillus* or *Humicola* (4), TAKA amylase of *Aspergillus oryzae*, alpha-amylase of *Aspergillus niger*, carboxyl peptidase of *Mucor* (U.S. Pat. No. 5,578,463), a lipase or proteinase from *Rhizomucor miehei*, cellobiohydrolase of *Trichoderma* (5), beta-galactosidase of *Penicillium canescens* and alpha mating factor of *Saccharomyces*.

Alternatively the signal sequence can be from an amylase or subtilisin gene of a strain of *Bacillus*. A signal sequence from the same genus as the host strain is extremely suitable as it is most likely to be specifically adapted to the specific host thus preferably the signal sequence is a signal sequence of *Chrysosporium*, especially of *Chrysosporium* strain C1, strain UV13-6, strain NG7C-19 and strain UV18-25, referred to above. Signal sequences from filamentous fungi, yeast and bacteria are useful. Signal sequences of non-fungal origin are also considered useful, particularly bacterial, plant and mammalian.

A recombinant host to be used according to any of the embodiments of the invention can further comprise a selectable marker. Such a selectable marker will permit easy selection of transformed or transfected cells. A selectable marker often encodes a gene product providing a specific type of resistance foreign to the non-transformed strain. This can be resistance to heavy metals, antibiotics and biocides in general. Prototrophy is also a useful selectable marker of the non-antibiotic variety. Non-antibiotic selectable markers can be preferred where the protein or polypeptide of interest is to be used in food or pharmaceuticals with a view to speedier or less complicated regulatory approval of such a product. Very often the GRAS indication is used for such markers. A number of such markers are available to the person skilled in the art. The FDA e.g. provides a list of such. Most commonly used are selectable markers selected from the group conferring resistance to a drug or relieving a nutritional defect e.g. the group comprising amdS (acetamidase), hph (hygromycin phosphotransferase), pyrG (orotidine-5'-phosphate decarboxylase), trpC (anthranilate synthase), argB (ornithine carbamoyltransferase), sC (sulphate adenyl-transferase), bar (phosphinothricin acetyltransferase), glufosinate resistance, niaD (nitrate reductase), a bleomycin resistance gene, more specifically Sh ble, sulfonylurea resistance e.g. acetolactate synthase mutation ilv1. Selection can also be carried out by virtue of cotransformation where the selection marker is on a separate vector or where the selection marker is on the same nucleic acid fragment as the polypeptide-encoding sequence for the polypeptide of interest.

As used herein the term heterologous polypeptide is a protein or polypeptide not normally expressed and secreted by the *Chrysosporium* host strain used for expression according to the invention. The polypeptide can be of plant or animal (vertebrate or invertebrate) origin e.g. mammalian, fish, insect, or micro-organism origin, with the proviso it does not occur in the host strain. A mammal can include a human. A micro-organism comprises viruses, bacteria, archae-bacteria and fungi i.e. filamentous fungi and yeasts. Bergey's Manual for Bacterial Determinology provides adequate lists of bacteria and archaebacteria. For pharmaceutical purposes quite often a preference will exist for human proteins thus a recombinant host according to the invention forming a preferred embodiment will be a host wherein the polypeptide is of human origin. For purposes such as food production suitably the heterologous polypeptide will be of animal, plant or algal origin. Such embodiments are therefore also considered suitable examples of the invention. Alternative embodiments that are useful also include a heterologous polypeptide of any of bacterial, yeast, viral, archaebacterial and fungal origin. Fungal origin is most preferred.

A suitable embodiment of the invention will comprise a heterologous nucleic acid sequence with adapted codon usage. Such a sequence encodes the native amino acid sequence of the host from which it is derived, but has a different nucleic acid sequence, i.e. a nucleic acid sequence in which certain codons have been replaced by other codons encoding the same amino acid but which are more readily used by the host strain being used for expression. This can lead to better expression of the heterologous nucleic acid sequence. This is common practice to a person skilled in the art. This adapted codon usage can be carried out on the basis of known codon usage of fungal vis-à-vis non-fungal codon usage. It can also be even more specifically adapted to codon usage of *Chrysosporium* itself. The similarities are such that codon usage as observed in *Trichoderma, Humicola* and *Aspergillus* should enable exchange of sequences of such organisms without adaptation of codon usage. Details are available to the skilled person concerning the codon usage of these fungi and are incorporated herein by reference.

The invention is not restricted to the above-mentioned recombinant *Chrysosporium* strains, but also covers a recombinant *Chrysosporium* strain comprising a nucleic acid sequence encoding a homologous protein for a *Chrysosporium* strain, said nucleic acid sequence being operably linked to an expression-regulating region and said recombinant strain expressing more of said protein than the corresponding non-recombinant strain under the same conditions. In the case of homologous polypeptide of interest such is preferably a neutral or alkaline enzyme like a hydrolase, a protease or a carbohydrate degrading enzyme as already described elsewhere. The polypeptide may also be acidic. Preferably the recombinant strain will express the polypeptide in greater amounts than the non-recombinant strain. All comments mentioned vis-à-vis the heterologous polypeptide are also valid (mutatis mutandis) for the homologous polypeptide cellulase.

Thus the invention also covers genetically engineered microbial strains wherein the sequence that is introduced can be of *Chrysosporium* origin. Such a strain can, however, be distinguished from natively occurring strains by virtue of for example heterologous sequences being present in the nucleic acid sequence used to transform or transfect the *Chrysosporium*, by virtue of the fact that multiple copies of the sequence encoding the polypeptide of interest are present or by virtue of the fact that these are expressed in an amount exceeding that of the non-engineered strain under identical conditions or by virtue of the fact that expression occurs under normally non-expressing conditions. The latter can be the case if an inducible promoter regulates the sequence of interest contrary to the non-recombinant situation or if another factor induces the expression than is the case in the non-engineered strain. The invention is directed at strains derived through engineering either using classical genetic technologies or genetic engineering methodologies.

The expression systems and host strains containing them according to the invention can comprise a nucleic acid sequence encoding a heterologous protein selected from carbohydrate-degrading enzymes (cellulases, xylanases, mannanases, mannosidases, pectinases, amylases, e.g. glucoamylases, α-amylases, α- and β-galactosidases, α- and β-glucosidases, β-glucanases, chitinases, chitanases), proteases (endoproteases, amino-proteases, amino- and carboxy-peptidases, keratinases), other hydrolases (lipases, esterases, phytases), oxidoreductases (catalases, glucose-oxidases) and transferases (transglycosylases, transglutaminases, isomerases and invertases).

The most interesting products to be produced according to invention are cellulases, xylanases, pectinases, lipases and proteases, wherein cellulases and xylanases cleave beta-1,4-bonds, and cellulases comprise endoglucanases, cellobiohydrolases and beta-glucosidases. These proteins are extremely useful in various industrial processes known in the art. Specifically for cellulases we refer e.g. to WO 98/15633 describing cellobiohydrolases and endoglucanases of use. The contents of said application are hereby incorporated by reference.

A recombinant according to the invention may have a nucleic acid sequence encoding the polypeptide of interest encodes a polypeptide that is inactivated or unstable at acid pH i.e. pH below 6, even below pH 5.5, more suitably even below pH 5 and even as low as or lower than pH 4. This is a particularly interesting embodiment, as the generally disclosed fungal expression systems are not cultured under conditions that are neutral to alkaline, but are cultured at acidic pH. Thus the system according to the invention provides a safe fungal expression system for proteins or polypeptides that are susceptible to being inactivated or are unstable at acid pH.

Quite specifically a recombinant strain as defined in any of the embodiments according to the invention, wherein the nucleic acid sequence encoding the polypeptide of interest encodes a protein or polypeptide exhibiting optimal activity and/or stability at a pH above 5, preferably at neutral or alkaline pH (i.e. above 7) and/or at a pH higher than 6, is considered a preferred embodiment of the invention. More than 50%, more than 70% and even more than 90% of optimal activities at such pH values are anticipated as being particularly useful embodiments. A polypeptide expressed under the cultivation conditions does not necessarily have to be active at the cultivation conditions, in fact it can be advantageous for it to be cultured under conditions under which it is inactive as its active form could be detrimental to the host. What is however required is for the protein or polypeptide to be stable under the cultivation conditions. The stability can be thermal stability. It can also be stability against specific compositions or chemicals, such as are present for example in compositions or processes of production or application of the polypeptide or protein of interest. LAS in detergent compositions comprising cellulases or lipases, etc. is an example of a chemical often detrimental to proteins. The time periods of use in applications can vary from short to long exposure so stability can be over a varying length of time varying per application. The skilled person will be able to ascertain the correct conditions on a case by case basis. One can use a number of commercially available assays to determine the optimal activities of the various enzymatic products. The catalogues of Sigma and Megazyme for example show such. Specific examples of tests are mentioned elsewhere in the description. The manufacturers provide guidance on the application.

A *Chrysosporium* strain can be suitably used to transform or transfect with the sequence of interest to be expressed and such a strain exhibits a relatively low biomass. We have found that *Chrysosporium* strains having a biomass two to five times lower than that of *Trichoderma reesei* when cultured to a viscosity of 200-600 cP at the end of fermentation and exhibiting a biomass of 10 to 20 times lower than that of *Aspergillus niger* when cultured to a viscosity of 1500-2000 cP under corresponding conditions, i.e. their respective optimal cultivation conditions can provide a high level of expression. This level of expression far exceeds that of the two commercial reference strains at a much lower biomass and at much lower viscosity. This means that the yield of expression of such *Chrysosporium* strains will be appreciably higher than from *Aspergillus niger* and *Trichoderma reesei*. Such a transformed or transfected *Chrysosporium* strain forms a suitable embodiment of the invention.

We find a biomass of 0.5-1.0 g/l for *Chrysosporium* strain C1(18-25) as opposed to 2.5-5.0 g/l for *Trichoderma reesei* and 5-10 g/l of *Aspergillus niger* under the above described conditions. In the Examples we provide details of this process.

In a suitable embodiment a recombinant *Chrysosporium* strain produces protein or polypeptide in at least the amount equivalent to the production in moles per liter of cellulase by the strain UV13-6 or C-19, and most preferably at least equivalent to or higher than that of the strain UV18-25 under the corresponding or identical conditions, i.e. their respective optimal cultivation conditions.

We have also found that expression and secretion rates are exceedingly high when using a *Chrysosporium* strain exhibiting the mycelial morphology of strain UV18-25 i.e. fragmented short mycelia. Thus a recombinant strain according to the invention will preferably exhibit such morphology. The invention however also covers non-recombinant strains or otherwise engineered strains of *Chrysosporium* exhibiting this novel and inventive characteristic. Also covered by the invention is a recombinant *Chrysosporium* strain in any of the embodiments described according to the invention further exhibiting reduced sporulation in comparison to C1, preferably below that of strain UV13-6, preferably below that of NG7C-19, preferably below that of UV18-25 under equivalent fermenter conditions. Also covered by the invention is a recombinant *Chrysosporium* strain in any of the embodiments described according to the invention further exhibiting at least the amount of protein production ratio to biomass in comparison to C1, preferably in comparison to that of any of strains UV13-6, NG7C-19 and UV18-25 under equivalent fermenter conditions. The invention however also covers non-recombinant strains or otherwise engineered strains of *Chrysosporium* exhibiting this novel and inventive characteristic as such or in combination with any of the other embodiments.

Another attractive embodiment of the invention also covers a recombinant *Chrysosporium* strain exhibiting a viscosity below that of strain NG7C-19, preferably below that of UV18-25 under corresponding or identical fermenter conditions. The invention however also covers non-recombinant strains or otherwise engineered strains of *Chrysosporium* exhibiting this novel and inventive characteristic as such or in combination with any of the other embodiments. We have determined that the viscosity of a culture of UV18-25 is below 10 cP opposed to that of *Trichoderma reesei* being of the order 200-600 cP, with that of *Aspergillus niger* being of the order 1500-2000 cP under their respective optimal culture conditions at the end of fermentation. The process used for such determination is provided in the examples.

Viscosity can be assessed in many cases by visual monitoring. The fluidity of the substance can vary to such a large extent that it can be nearly solid, sauce-like or liquid. Viscosity can also readily be ascertained by Brookfield rotational viscometry, use of kinematic viscosity tubes, falling ball viscometer or cup type viscometer. The yields from such a low viscosity culture are higher than from the commercial known higher viscosity cultures per time unit and per cell.

The processing of such low viscosity cultures according to the invention is advantageous in particular when the cultures are scaled up. The subject *Chrysosporium* strains with the low viscosity perform very well in cultures as large as up to 150,000 liter cultures. Thus any culture size up to 150,000 liters provides a useful embodiment of the invention. Any other conventional size of fermentation should be carried out well with the strains according to the invention. The reasoning behind this is that problems can arise in large scale production with the formation of aggregates that have mycelia that are too dense and/or are unevenly distributed. The media as a result cannot be effectively utilised during the culture thus leading to an inefficient production process in particular in large scale fermentations i.e. over 150,000 liters. Aeration and mixing become problematic leading to oxygen and nutrient starvation and thus reduced concentration of productive biomass and reduced yield of polypeptide during the culture and/or can result in longer fermentation times. In addition high viscosity and high shear are not desirable in commercial fermentation processes and in current commercial processes they are the production limiting factors. All these negative aspects can be overcome by the *Chrysosporium* host according to the invention which exhibits much better characteristics than *Trichoderma reesei, Aspergillus niger* and *Aspergillus oryzae* that are commercially used in this respect i.e. exhibits better protein production levels and viscosity properties and biomass figures.

A *Chrysosporium* strain according to any of the above-mentioned embodiments of the invention, said strain further exhibiting production of one or more of the fungal enzymes selected from the carbohydrate-degrading enzymes, proteases, other hydrolases, oxidoreductase, and transferases mentioned above, is considered a particularly useful embodiment of the invention. The most interesting products are specifically cellulases, xylanases, pectinases, lipases and proteases. Also useful as embodiment of the invention however is a *Chrysosporium* strain exhibiting production of one or more fungal enzymes that exhibit neutral or alkaline optimal stability and/or activity, preferably alkaline optimal stability and/or activity, said enzyme being selected from carbohydrate-degrading enzymes, hydrolases and proteases, preferably hydrolases and carbohydrate-degrading enzymes. In the case of non-recombinant *Chrysosporium*, such enzymes are suitably other than cellulase as disclosed in WO 98/15633. Enzymes of particular interest are xylanases, proteases, esterases, alpha galactosidases, beta-galactosidases, beta-glucanases and pectinases. The enzymes are not limited to the aforementioned. The comments vis-à-vis stability and activity elsewhere in the description are valid here also.

The invention also covers a method of producing a polypeptide of interest, said method comprising culturing a host strain (e.g. fungal such as of the genera *Chrysosporium, Aspergillus, Trichoderma, Hansenula, Mucor, Pichia, Neurospora, Tolypocladium, Rhizomucor, Fusarium, Penicillium* or bacterial or other microbial) in any of the embodiments according to the invention under conditions permitting expression and preferably secretion of the polypeptide and recovering the subsequently produced polypeptide of interest.

Where protein or polypeptide is mentioned, variants and mutants e.g. substitution, insertion or deletion mutants of naturally occurring proteins are intended to be included that exhibit the activity of the non-mutant. The same is valid vis-à-vis the corresponding nucleic acid sequences. Processes such as gene shuffling, protein engineering and directed evolution site directed mutagenesis and random mutagenesis are processes through which such polypeptides, variants or mutants can be obtained. U.S. Pat. No. 5,223,409, U.S. Pat. No. 5,780,279 and U.S. Pat. No. 5,770,356 provide teaching of directed evolution. Using this process a library of randomly mutated gene sequences created for example by gene shuffling via error prone PCR occurs in any cell type. Each gene has a secretion region and an immobilising region attached to it such that the resulting protein is secreted and stays fixed to the host surface. Subsequently conditions are created that necessitate the biological activity of the particular polypeptide. This occurs for a number of cycles ultimately leading to a final gene with the desired characteristics. In other words a speeded up directed process of evolution. U.S. Pat. No. 5,763,192 also describes a process for obtaining DNA, RNA, peptides, polypeptides or protein by way of synthetic polynucleotide coupling stochastically generated sequences, introduction thereof into a host followed by selection of the host cell with the corresponding predetermined characteristic.

Another application of the method of the present invention is in the process of "directed evolution", wherein novel protein-encoding DNA sequences are generated, the encoded proteins are expressed in a host cell, and those sequences encoding proteins having a desired characteristic are mutated and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780,279 and 5,770,356 provide teaching of directed evolution. See also Kuchner and Arnold, *Trends in Biotechnology,* 15:523-530 (1997); Schmidt-Dannert and Arnold, *Trends in Biotech.,* 17-135-136 (1999); Arnold and Volkov, *Curr. Opin. Chem. Biol.,* 3:54-59 (1999); Zhao et al., *Manual of Industrial Microbiology and Biotechnology,* 2nd Ed., (Demain and Davies, eds.) pp. 597-604, ASM Press, Washington D.C., 1999; Arnold and Wintrode, *Encyclopedia of Bioprocess Technology: Fermentation, Biocatalysis, and Bioseparation*, (Flickinger and Drew, eds.) pp. 971-987, John Wiley & Sons, New York, 1999; and Minshull and Stemmer, *Curr. Opin. Chem. Biol.* 3:284-290.

An application of combinatorial mutagenesis is disclosed in Hu et al., Biochemistry. 1998 37:10006-10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., *Nucleic Acids Res.,* 26:681-683 (1998)), the staggered extension process (H. Zhao et al., *Nature Biotech.,* 16:258-262 (1998)), and heteroduplex recombination (A. Volkov et al., *Nucleic Acids Res.,* 27:e18 (1999)). Error-prone PCR is yet another approach (Song and Rhee, Appl. *Environ. Microbiol.* 66:890-894 (2000)).

There are two widely-practised methods of carrying out the selection step in a directed evolution process. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow on cellulose at pH 8 are obtained. Thermostable variants of enzymes can likewise be evolved, by cycles of gene mutation and high-temperature culturing of host cells (Liao et al., *Proc. Natl. Acad. Sci. USA* 83:576-580 (1986); Giver et al., *Proc. Natl. Acad. Sci. USA* 95:12809-12813 (1998).

An alternative to the massively parallel "survival of the fittest" approach is serial screening. In this approach, individual transformants are screened by traditional methods, such as observation of cleared or coloured zones around colonies growing on indicator media, calorimetric or fluorometric enzyme assays, immunoassays, binding assays, etc. See for example Joo et al., Nature 399:670-673 (1999), where a cytochrome P450 monooxygenase not requiring NADH as a cofactor was evolved by cycles of mutation and screening; May et al., *Nature Biotech.* 18:317-320 (2000), where a hydantoinase of reversed stereoselectivity was evolved in a similar fashion; and Miyazaki et al., *J. Mol. Biol.* 297:1015-1026 (2000), where a thermostable subtilisin was evolved.

Standard cloning and protein or polypeptide isolation techniques can be used to arrive at the required sequence information. Parts of known sequences can be used as probes to isolate other homologues in other genera and strains. The nucleic acid sequence encoding a particular enzyme activity can be used to screen a *Chrysosporium* library for example. A person skilled in the art will realise which hybridisation conditions are appropriate. Conventional methods for nucleic acid hybridisation construction of libraries and cloning techniques are described in Sambrook et al (Eeds) (1989) In "Molecular Cloning. A Laboratory Manual" Cold Spring Harbor, Press Plainview, N.Y., and Ausubel et al (Eds) "Current Protocols in Molecular Biology" (1987) John Wiley and Sons, New York. The relevant information can also be derived from later handbooks and patents, as well as from various commercially available kits in the field.

In an alternative embodiment, said method comprises culturing a strain according to the invention under conditions permitting expression and preferably secretion of the protein or polypeptide or precursor thereof and recovering the subsequently produced polypeptide and optionally subjecting the precursor to additional isolation and purification steps to obtain the polypeptide of interest. Such a method may suitably comprise a cleavage step of the precursor into the polypeptide or precursor of interest. The cleavage step can be cleavage with a Kex-2 like protease, any basic amino acid paired protease or Kex-2 for example when a protease cleavage site links a well secreted protein carrier and the polypeptide of interest. A person skilled in the art can readily find Kex-2-like protease sequences as consensus sequence details for such are available and a number of alternatives have already been disclosed e.g. furin.

Suitably in a method for production of the polypeptide according to any of the embodiments of the invention the cultivation occurs at pH higher than 5, preferably 5-10, more preferably 6-9. Suitably in such a method the cultivation occurs at a temperature between 25-43° C., preferably 30-40° C. The strain used in the method according to the invention is quite suitably a recombinant *Chrysosporium* strain or other fungal or non-fungal strain. The method according to the invention in such a case can further be preceded by the step of production of a recombinant strain according to the invention. The selection of the appropriate conditions will depend on the nature of the polypeptide to be expressed and such selection lies well within the realm of normal activity of a person skilled in the art.

The method of production of a recombinant strain according to the invention is also part of the subject invention. The method comprises stably introducing a nucleic acid sequence encoding a heterologous or homologous polypeptide into a suitable host strain, said nucleic acid sequence being operably linked to an expression regulating region, said introduction occurring in a manner known per se for transforming filamentous fungi. As stated above numerous references hereof are available and a small selection has been cited. The information provided is sufficient to enable the skilled person to carry out the method without undue burden. The method comprises introduction of a nucleic acid sequence comprising any of the nucleic acid elements described in the various embodiments of the recombinant strain according to the invention as such or in combination.

By way of example the introduction can occur using the protoplast transformation method. The method is described in the examples. Alternative protoplast or spheroplast transformation methods are known and can be used as have been described in the prior art for other filamentous fungi. Details of such methods can be found in many of the cited references and are thus incorporated by reference. A method according to the invention suitably comprises using a non-recombinant strain as starting material for introduction of the desired sequence encoding the polypeptide of interest.

The subject invention also covers a method of producing *Chrysosporium* enzyme, said method comprising culturing a *Chrysosporium* or other strain in or on a cultivation medium at pH higher than 5, preferably 5-10, more preferably 6-9, suitably 6-7.5, 7.5-9 as examples of neutral and alkaline pH ranges.

More in general the invention further covers a method of producing enzymes exhibiting neutral or alkaline optimal activity and/or stability, preferably alkaline optimal activity and/or stability. The preferred ranges vis-à-vis pH and optimal activity as well as assays with which to determine such have been provided elsewhere in the description. The enzyme should be selected from carbohydrate-degrading enzymes, proteases, other hydrolases, oxidoreductases, and transferases, as described above, said method comprising cultivating a host cell transformed or transfected with the corresponding enzyme-encoding nucleic acid sequence. Suitably such an enzyme will be a *Chrysosporium* enzyme. A suitable method such as this comprises production specifically of cellulase, xylanase, pectinase, lipase and protease, wherein cellulase and xylanase cleave β-1,4-bonds and cellulase comprises endoglucanase, cellobiohydrolase and β-glucosidase. The method according to the invention can comprise cultivating any *Chrysosporium* host according to the invention comprising nucleic acid encoding such aforementioned enzymes. Suitably the production of non-recombinant *Chrysosporium* hosts according to the invention is directed at production of carbohydrate degrading enzymes, hydrolases and proteases. In such a case the enzyme is suitably other than a cellulase.

Methods of isolating are analogous to those described in WO 98/15633 and are incorporated by reference.

The enzymes produced according to the invention are also covered by the invention. Enzymes of *Chrysosporium* origin as can be isolated from non-recombinant *Chrysosporium* strains according to the invention are also covered. They exhibit the aforementioned stability, activity characteristics. Suitably they are stable in the presence of LAS. In particular proteases with pI 4-9.5, proteases with a MW of 25-95 kD, xylanases with pI between 4.0 and 9.5, xylanases with MW between 25 and 65 kD, endoglucanases with a pI between 3.5 and 6.5, endoglucanases with MW of 25-55 kDa, β-glucosidases, α,β-galactosidases with a pI of 4-4.5, β-glucosidases, α,β-galactosidases with a MW of 45-50 kDa, cellobiohydrolases of pI 4-5, cellobiohydrolases of MW 45-75 kDa, e.g. a MW of 55 kD and pI 4.4, polygalacturonases, with a pI of 4.0-5.0 polygalacturonase of 60-70 kDa, e.g. 65⁻kDa, esterases with a pI 4-5, and esterases with a MW of 95-105 kDa with the aforementioned stability, activity characteristics are claimed. The molecular weights (MW) are those determined by SDS-PAGE. The non-recombinant i.e. natively occurring enzyme is other than cellulase as disclosed in WO 98/15633. Enzymes with combinations of the p1 values and molecular weights mentioned above are also covered.

The invention is also concerned with the (over)production of non-protein products by the mutant (recombinant) strains of the invention. Such non-protein products include primary metabolites such as organic acids, amino acids, and secondary such as antibiotics, e.g. penicillins and cephalosporins and other therapeutics. These products are the result of combinations of biochemical pathways, involving several fungal genes of interest. Fungal primary and secondary metabolites and procedures for producing these metabolites in fungal organisms are well known in the art. Examples of the production of primary metabolites have been described by Mattey M., The Production of Organic Acids, *Current Reviews in Biotechnology,* 12, 87-132 (1992). Examples of the production of secondary metabolites have been described by Penalva et al. The Optimization of Penicillin Biosynthesis in Fungi, *Trends in Biotechnology* 16, 483-489 (1998).

EXAMPLES

Examples of Transformation Comparing *Chrysosporium, Trichoderma* and *Tolypocladium* Geodes Two untransformed *Chrysosporium* C1 strains and one *Trichoderma reesei* reference strain were tested on two media (Gs pH 6.8 and Pridham agar, PA, pH 6.8). To test the antibiotic resistance level spores were collected from 7 day old PDA plates. Selective plates were incubated at 32° C. and scored after 2.4 and 5 days. It followed that the C-1 strains NG7C-19 and UV18-25 clearly have a low basal resistance level both to phleomycin and hygromycin. This level is comparable to that for a reference *T. reesei* commonly used laboratory strain. Thus there is clear indication these two standard fungal selectable markers can be used well in *Chrysosporium* strains. Problems with other standard fungal selectable markers should not be expected.

Selection of Sh-ble (phleomycin-resistance) transformed *Chrysosporium* strains was succesfully carried out at 50 μg/ml. This was also the selection level used for *T. reesei* thus showing that differential selection can be easily achieved in *Chrysosporium*. The same comments are valid for transformed strains with hygromycin resistance at a level of 150 μg/ml.

The protoplast transformation technique was used on *Chrysosporium* based on the most generally applied fungal transformation technology. All spores from one 90 mm PDA plate were recovered in 8 ml IC1 and transferred into a shake flask of 50 ml IC1 medium for incubation for 15 hours at 35° C. and 200 rpm. After this the culture was centrifuged, the pellet was washed in MnP, brought back into solution in 10 ml MnP and 10 mg/ml Caylase $C_3$ and incubated for 30 minutes at 35° C. with agitation (150 rpm).

The solution was filtered and the filtrate was subjected to centrifugation for 10 minutes at 3500 rpm. The pellet was washed with 10 ml $MnPCa^{2+}$. This was centrifuged for 10 minutes at 25° C. Then 50 microliters of cold MPC was added. The mixture was kept on ice for 30 minutes whereupon 2.5 ml PMC was added. After 15 minutes at room temperature 500 microliters of the treated protoplasts were mixed to 3 ml of MnR Soft and immediately plated out on a MnR plate containing phleomycin or hygromycin as selection agent. After incubation for five days at 30° C. transformants were analysed (clones become visible after 48 hours). Transformation efficiency was determined using 10 microgrammes of reference plasmid pAN8-1[19]. The results are presented in the following Table 1.

TABLE 1

Transformation efficiency (using 10 μg of reference plasmid pAN8-1)

| | *T. reesei* | NG7C-19 | UV18-25 |
|---|---|---|---|
| Viability | $10^6$/200 μl | 5 $10^6$/200 μl | 5 $10^6$/200 μl |
| Transformants Per 200 μl | 2500 | $10^4$ | $10^4$ |
| Transformants per $10^6$ viable cells | 2500 | 2000 | 2000 |

The *Chrysosporium* transformant's viability is superior to that of *Trichoderma*. The transformability of the strains is comparable and thus the number of transformants obtained in one experiment lies 4 times higher for *Chrysosporium* than for *T. reesei*. Thus the *Chrysosporium* transformation system not only equals the commonly used *T. reesei* system, but even outperforms it. This improvement can prove especially useful for vectors that are less transformation efficient than pAN8-1. Examples of such less efficient transformation vectors are protein carrier vectors for production of non-fungal proteins which generally yield 10 times fewer transformants.

A number of other transformation and expression vectors were constructed with homologous *Chrysosporium* protein encoding sequences and also with heterologous protein encoding sequences for use in transformation experiments with *Chrysosporium.*

Examples of expression systems include a *Chrysosporium* xylanase Xyl1 promoter fragment linked to a xylanase signal sequence in frame with a xylanase open reading frame followed by a xylanase terminator sequence. Transformant selection is carried out by using cotransformation with a selectable vector.

Another example is a *Chrysosporium lucknowense* cellobiohydrolase promoter linked to *Penicillium* endoglucanase 3 signal sequence in frame with the *Penicillium* endoglucanase 3 open reading frame followed by the *Chrysosporium* cellobiohydrolase terminator sequence. In addition this vector carries a second expression cassette with a selection marker i.e. the aceetamidase S gene (AmdS gene).

A further example comprises *Chrysosporium* glyceraldehyde-3-phosphate dehydrogenase 1 promoter linked to the *Aspergillus niger* glucoamylase signal sequence and the glucoamylase open reading frame fused to the human Interleukine 6 open reading frame. In adddition this vector carries a second expression cassette with a selection marker i.e. the AmdS gene.

A still further example is a *Aspergillus nidulans* glyceraldehyde-3-phosphate dehydrogenase A promoter linked to the endoglucanase 5 open reading frame followed by a *Aspergillus nidulans* terminator sequence.

Examples of Heterologous and Homologous Expression of *Chrysosporium* Transformants C1 strains (NG7C-19 and/or UV18-25) have been tested for their ability to secrete various heterologous proteins: a bacterial protein (*Streptoalloteichus hindustanus* phleomycin-resistance protein, Sh ble), a fungal protein (*Trichoderma reesei* xylanase II, XYN2) and a human protein (the human lysozyme, HLZ).

C1 secretion of *Trichoderma reesei* xylanase II (XYN2).

C1 strain UV18-25 has been transformed by the plasmids pUT1064 and pUT1065. pUT1064 presents the two following fungal expression cassettes:

The first cassette allows the selection of phleomycin-resistant transformants:

*Neurospora crassa* cross-pathway control gene 1 (cpc-1) promoter[14]

*Streptoalloteichus hindustanus* phleomycin-resistance gene Sh ble[4]

*Aspergillus nidulans* tryptophan-synthase (trpC) terminator[5]

The second cassette is the xylanase production cassette:

*T. reesei* strain TR2 cbh1 promoter[15]

*T. reesei* strain TR2 xyn2 gene (including its signal sequence)[16]

*T. reesei* strain TR2 cbh1 terminator[15]

The vector also carries an *E. coli* replication origin from plasmid pUC19[6]. The plasmid detailed map is provided in FIG. 1.

pUT1065 presents the following fungal expression cassette:

*A. nidulans* glyceraldehyde-3-phosphate dehydrogenase (gpdA) promoter[2]

A synthetic *T. reesei* cellobiohydrolase I (cbh1) signal sequence[1,3]

*S. hindustanus* phleomycin-resistance gene Sh ble[4] used as carrier-protein[10]

A linker peptide (SGERK) (SEQ ID NO: 8) featuring a KEX2-like protease cleavage site[1]

*T. reesei* strain TR2xyn2 gene (without signal sequencel[16]

*A. nidulans* tryptophan-synthase (trpC) terminator[5]

The vector also carries the beta-lactamase gene (bla) and an *E. coli* replication origin from plasmid pUC18[6]. The plasmid detailed map is provided in FIG. 2.

C1 protoplasts were transformed with plasmid pUT1064 or pUT1065 following the same procedure already described in the above example. The fusion protein in plasmid pUT1065 (Sh ble::XYN2) is functional with respect to the phleomycin resistance thus allowing easy selection of the C1 transformants. Moreover, the level of phleomycin resistance correlates roughly with the level of xyn2 expression. In pUT1064, xyn2 was cloned with its own signal sequence.

The xylanase production of C1 transformants (phleomycin-resistant clones) was analysed by xylanase activity assay as follows: Primary transformants were toothpicked to GS+phleomycin (5 μg/ml) plates (resistance verification) and also on XYLAN plates (xylanase activity detection by clearing zone visualisation[17]). Plates were grown for 5 days at 32° C. Each validated clone was subcloned onto XYLAN plates. Two subclones per transformant were used to inoculate PDA plates in order to get spores for liquid culture initiation. The liquid cultures in IC1+5 g/l KPhtalate were grown 5 days at 27° C. (shaking 180 rpm). Then, the cultures were centrifuged (5000 g, 10 min.). From these samples, xylanase activity was measured by DNS technique according to Miller et al.[18]

TABLE 2

Active XYN2 production levels in C1 (best producers)

| | Active xylanase II concentration in culture media | Xylanase II specific activity in culture media |
|---|---|---|
| Untransformed UV18-25 | 3.9 U./ml | 3.8 U./mg total prot. |
| UV18-25::1064 clone 7-1 | 4.7 U./ml | 4.7 U./mg total prot. |
| UV18-25::1064 clone 7-2 | 4.4 U./ml | 4.3 U./mg total prot. |
| UV18-25::1065 clone 1-1 | 29.7 U./ml | 25.6 U./mg total prot. |
| UV18-25::1065 clone 1-2 | 30.8 U./ml | 39.4 U./mg total prot. |

These data show that:

1) Points 1 to 4 from example 2 are confirmed.

2) C1 can be used as host for the secretion of a heterologous fungal protein.

Appendix to the Examples

Media

Transformation media:

| | | | |
|---|---|---|---|
| Mandels Base: | MaP Medium: | | |
| $KH_2PO_4$ | 2.0 g/l | Mandels Base with | |
| $(NH_4)_2SO_4$ | 1.4 g/l | Peptone 1 g/l | |
| $MgSO_4 \cdot 7H_2O$ | 0.3 g/l | MES 2 g/l | |
| $CaCl_2^-$ | 0.3 g/l | Sucrose 100 g/l | |
| Oligoelements | 1.0 ml/l | Adjust pH to 5 | |
| MnR | MnP $CA^{2+}$: | | |
| MnP + sucrose | 130 g/l | MnP Medium+ | |
| Yeast extract | 2.5 g/l | $CaCl_2$ $2H_2O$ | 50 mM |
| Glucose | 2.5 g/l | Adjust pH to 6.5 | |
| Agar | 15 g/l | | |
| MnR Soft: | MnR with only 7.5 g/l of agar. | | |
| MPC: | | | |
| $CaCl_2$ | 50 mM | pH 5.8 | |
| MOPS | 10 mM | | |
| PEG | 40% | | |

For selection and culture

| | | |
|---|---|---|
| GS: | | |
| Glucose | 10 g/l | |
| Biosoyase | 5 g/l | [Merieux] |
| Agar | 15 g/l | pH should be 6.8 |
| PDA: | | |
| Potato Dextrose Agar | 39 g/l | [Difco] pH should be 5.5 |
| MPG: | | |
| Mandels Base with | | |
| K.Phtalate | 5 g/l | |
| Glucose | 30 g/l | |
| Yeast extract | 5 g/l | |

The regeneration media (MnR) supplemented with 50 µg/ml phleomycin or 100-150 µg/ml hygromycin is used to select transformants. GS medium, supplemented with 5 µg/ml phleomycin is used to confirm antibiotic resistance.

PDA is a complete medium for fast growth and good sporulation. Liquid media are inoculated with 1/20th of spore suspension (all spores from one 90 mm PDA plate in 5 ml 0.1% Tween). Such cultures are grown at 27° C. in shake flasks (200 rpm).

Isolation and Characterisation of C1 Genes and Gene Expression Sequences of CBH1, XYL1, and GPD Construction of a BlueSTAR gene library of UV18-25

Chromosomal DNA of UV18-25 was partially digested with Sau3A, fragments of 12-15 kb were isolated and ligated in a BamHI site of cloning vector BlueSTAR. Packaging of 20% of the ligation mixture resulted in a gene library of $4.6\times10^4$ independent clones. This library was multiplied and stored at 4° C. and −80° C. The rest of the ligation mixture was also stored at 4° C.

Screening the gene library of UV18-25 for isolation of the genes for cbh1, xyl1 and gpd1 For the isolation of the different genes, in total $\pm7.5\times10^4$ individual BlueSTAR phages per probe were hybridised in duplo. Hybridisation was carried out with the PCR fragments of cbh1, and xyl1 (as described in WO 00/20555) at homologous conditions (65° C.; 0.2×SSC) and with the gpd1 gene of *A. niger* at heterologous conditions (53° C.; 0.5×SSC). The number of positive signals is given in Table 3. The positive clones were rescreened and for each clone two individual phages were used for further experiments. DNA of the different clones was analysed by restriction analysis to determine the number of different clones isolated from each gene (results are given in Table 3).

As for each of the 3 genes, 4-6 different clones were isolated, we conclude that the primary gene library ($\pm$4-$5\times10^4$ clones) represents about 5x genome of UV18-25. From this result we conclude that the complete genome of UV18-25 is represented in $9\times10^3$ clones. Based on an average genomic insert of 13 kb, this would indicate a genome size of ±120 Mb, which is 3 times the size of the *Aspergillus* genome.

PCR reactions with specific primers for the gene present on the plasmid (based on previous sequence determination from the isolated PCR fragments) and the T7 and T3 primer present in the polylinker of pBlueSTAR we were able to determine the location of the genes in a number of clones. From each gene a plasmid was used for sequence determination of the gene.

TABLE 3

Screening of $7.5\times10^4$ phages of the gene library of UV18-25 with PCR fragments of UV18-25 for the cbh1 gene and the xyl1 gene (homologous conditions) and with the gpdA gene of *A. niger* (heterologous conditions). DNA isolation and restriction analysis was used to determine number of different clones.

| Gene | Positive in first screening | positive in rescreening | different clones | clone used for sequencing |
|---|---|---|---|---|
| cbh1 | 8 | 7 | 4 | pCBH7 |
| xyl1 | 9 | 6 | 5 | pXyl5 |
| gpd1 | 12 | 12 | 6 | pGPD4 |

Sequence Analysis of the Cloned Genes

For the cbh1, xyl1, and the gpd1 gene, the results of the sequence determination are represented in SEQ ID No's 1, 3 and 5 respectively. Also the deduced amino acid sequences of the proteins are represented in these SEQ ID No's 2, 4 and 6. Some properties of the proteins are given in Table 4. It should be mentioned that the position of the start of the translation and the introns is based on homology with genes from the same family (i.e. paper genetics).

CBH1

From the amino acid sequences of CBH1, we concluded that the protein is about 63 kD in size and that a cellulose-binding domain (CBD) is present at the C-terminal part of the protein. Interestingly, no evidence was found for the presence of a CBD in the isolated 55 kD major protein. However, the presence of the isolated peptides from this 55 kD major protein in the encoded CBH1 protein (SEQ ID No. 1, 2), confirms that the 55 kD protein is encoded by the cloned gene. A possible explanation of these results is that the 55 kD protein is a truncated version of the CBH1 protein lacking the CBD.

The cellobiohydrolase CBH1 has activity against MUF-cellobioside, MUF lactoside, FP and avicel, also against p-nitrophenyl β-glucoside, cellobiose and p-nitrophenyl lactoside. Its activity toward MUF cellobioside is inhibited by cellobiose with inhibition constant of 0.4 mM. The Michaelis constant toward MUF cellobioside was 0.14 mM, toward MUF lactoside was 4 mM and toward CMC was 3.6 g/l. The pH optimum is from 4.5 to 7.50% of maximum activity toward CMC and 80% activity toward RBB-CMC is kept at pH 8.70-80% activity within pH 5-8 is kept during 25 hours of incubation. The temperature optimum is 60-70° C. CBH1 is a member of the cellobiohydrolase family 7. The corresponding CBH promoter, which is a preferred embodiment of the invention, is indicated in SEQ ID No. 1.

Xyl1

From the amino acid sequences of Xyl1 we conclude that also here a CBD is present, in this protein at the N-terminal side (i.e. directly attached to or at less than 5 amino acids distance from the signal sequence). In the literature only few more xylanases with a CBD are known (*Fusarium oxysporum, Humicola grisea* and *Neocallimastix patriciarum*). The estimated size of the Xyl1 protein is 43 kD and several peptides isolated from a 30 kD xylanase originate from this protein (SEQ ID No. 3, 4). Several isolated peptides could not be found in the encoded sequence. This could indicate that alternative xylanase proteins are present in UV18-25. In previous analyses, no evidence was found for the presence of CBD in this 30 kD protein. Also from these results we hypothesized that the CBD of the protein is cleaved off by proteolysis. This hypothesis will be analysed further (by determination of activities, N-terminal sequences and sizes of the different proteins in the different C1 strains: C1 wild type, NG7C, UV13-6, UV18-25 and protease mutants of UV18-25). Also the effect of the presence or absence of the CBD on enzymatic activities is analysed in more detail. Overexpression of the full length genes in various C1 hosts may be considered.

The presence of a cellulose-binding domain (CBD) is a particular feature of this enzyme. The only other known family 10 glycolytic enzyme (xylanase) having an N-terminal CBD is the *Fusarium oxysporum* XylF. The CBD of the *Chrysosporium lucknowense* Xyl1 protein has the sequence: WGQCG GQGWT GPTTC VSGAV CQFVN DWYSQ CV (amino acids 22-53 of SEQ ID No. 4). This sequence does not comply to the CBD consensus sequence described in U.S. Pat. No. 5,763,254 (Novo).

This consensus sequence of U.S. Pat. No. 5,763,254 is: W/Y-G/A-Q-C-G G-Q/I/N-G/N-W/F/Y-S/T/N/Q G-P/A/C-T/R/K-T/C/N-C X-X-G/P-S/T/F/L/A/--T/K C-V/T/R/E/K-K/Q/A-Q/-Q/I-N Q/D/A-W/F/Y-Y-Y/S/H/A-Q C-L/I/Q/V/T (SEQ ID NO:7), wherein W/Y means either W or Y etc., X means any amino acid, and—means absent. Four differences with the most degenerate consensus sequence are present in Xyl1, which are underlined in sequence 7 above. The invention thus pertains to xylanases having an N-terminal CBD different from this consensus CBD and other than the *Fusarium oxysporum* xylanase. More particularly the xylanase of the invention has a CBD having at least 55%, especially at least 65%, preferably at least 75% sequence identity with the sequence 7 above. Preferably the CBD contains one of the amino acids Phe, Tyr and Trp at position 23, or at least one of the four amino acids Val at position 20, Gln at position 22, Phe at position 23, Val at position 24. Preferred sequences comprise Cys-Xaa-Phe, Xaa-Phe-Val, Cys-Xaa-Phe-Val (SEQ ID NO:11), Cys-Gln-Phe, Val-Cys-Xaa-Phe (SEQ ID NO:12), Gln-Phe-Val, Gln-Trp-Val, Gln-Tyr-Val, Val-Cys-Gln, Val-Cys-Gln-Phe (SEQ ID NO: 9) and Val-Cys-Xaa-Phe-Val (SEQ ID NO:10), wherein Xaa is any amino acid or preferably Val, Thr, Arg, Glu, Gln or Lys, or most preferably Gln or Glu.

The xylanase does not possess MUF cellobiase activity and is thus a true xylanase. It possesses high activity within a broad pH range from 5-8 maintaining 65% of maximum activity at pH 9-10; it is a member of the xylanase F family. The corresponding xylanase promoter, which is a preferred embodiment of the invention, is shown in SEQ ID No. 3. The Michaelis constant towards birch xylan is 4.2 g/l for the 30 kD xylanase. Temperature optimum was high and equal to 70° C. for the xylanase.

Gpd1

The DNA sequence of the C-terminal part of the gpd1 gene is not determined. The promoter sequences of this gene is a preferred embodiment of the present invention and is depicted in SEQ ID No. 5.

The expression level of four *Chrysosporium* genes was studied by Northern analysis. Various strains of *C. lucknowense* were grown in rich medium containing pharmedia with cellulose and lactose (medium 1) or rich medium containing pharmedia and glucose (medium 2) at 33° C. After 48 h, mycelium was harvested and RNA was isolated. The RNA was hybridised with 4 different probes: EG5, EG6, Xyl1 and CBH. After exposure, the Northern blots were stripped and hybridised again with a probe for ribosomal L3 as a control for the amount of mRNA on the blot. Most strains showed very high response for CBH and high response for Xyl1 in medium 1; in medium 2, half of the strain showed high response for all genes, and the other half showed low response. The order of expression strength was deducted from these data as CBH>Xyl1>EG5>EG6.

The protein Xyl1 of *C. lucknowense* is 67% identical (72% homologous) to its closest homologue in the Genbank DATABASE (Table 4). The strong homology of the CBH1 protein to its related *Humicola grisea* homologue (74% identical/82% homologous) is noteworthy. It is also noted that in all cases the closest homologues originate from *Fusarium, Humicola* or other Pyrenomycetous (Sordariamycetous) fungi (Table 4), whereas *Chrysosporium* belongs to the Plectomycetous (Eurotiomycetous) fungi according to the NCBI database (Table 4). Thus the invention also pertains to glycanolytic enzymes, especially cellobiohydrolases and xylanases comprising a CBD, derived from plectomycetous fungi.

TABLE 4

Structural and comparative data of CBH1, Xyl1, and GPD1 of the invention.

| | glyco-sidase family | isolated from C1 | number of amino acids | introns | remarks | related sequences (% identity/% homology) |
|---|---|---|---|---|---|---|
| CBH1 | 7 | 70 kD<br>55 kD | 526<br>(63 kD) | 1 | CBD | *Humicola grisea* (74/82)<br>(CBH1:P15828)<br>*Fusarium oxysporum* (58/68)<br>(CBH: P46238)<br>*Neurospora crassa* (60/69)<br>(CBH1: P38676) |
| XYL1 | 10 | 30 kD | 333<br>(43 kD) | 3 | CBD | *Fusarium oxysporum* (67/72)<br>(XylF: P46239)<br>*Penicillium simplissicum* (63/72)<br>(XylF: P56588)<br>*Aspergillus aculeatus* (61/70)<br>(XylF: O59859) |
| GPD1 | — | — | Incomplete | 2+? | — | *Podospora anserina* (85/89)<br>(GPD: P32637)<br>*Neurospora crassa* 80/86)<br>(GPD: U67457)<br>*Cryphonectria parasitica* 80/85)<br>(GPD: P19089) |

REFERENCES

The Contents Hereof are Incorporated

Figure 1:
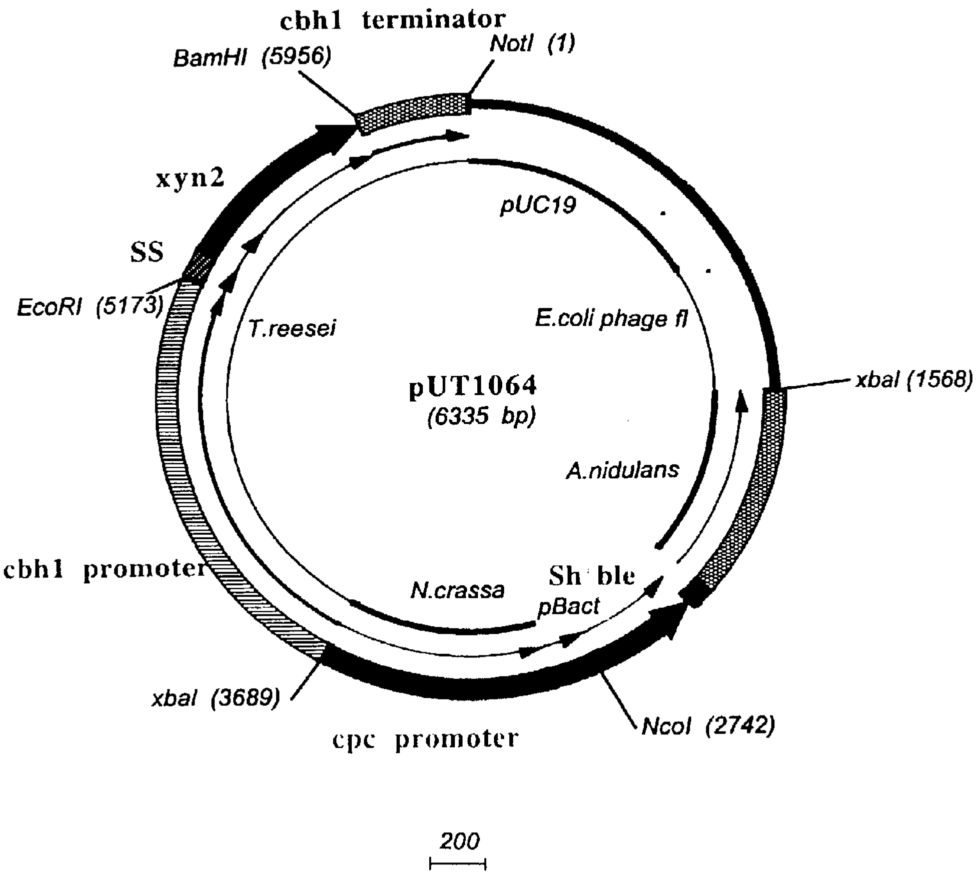
FIG. 1 is a pUT1064 map
Figure 2:
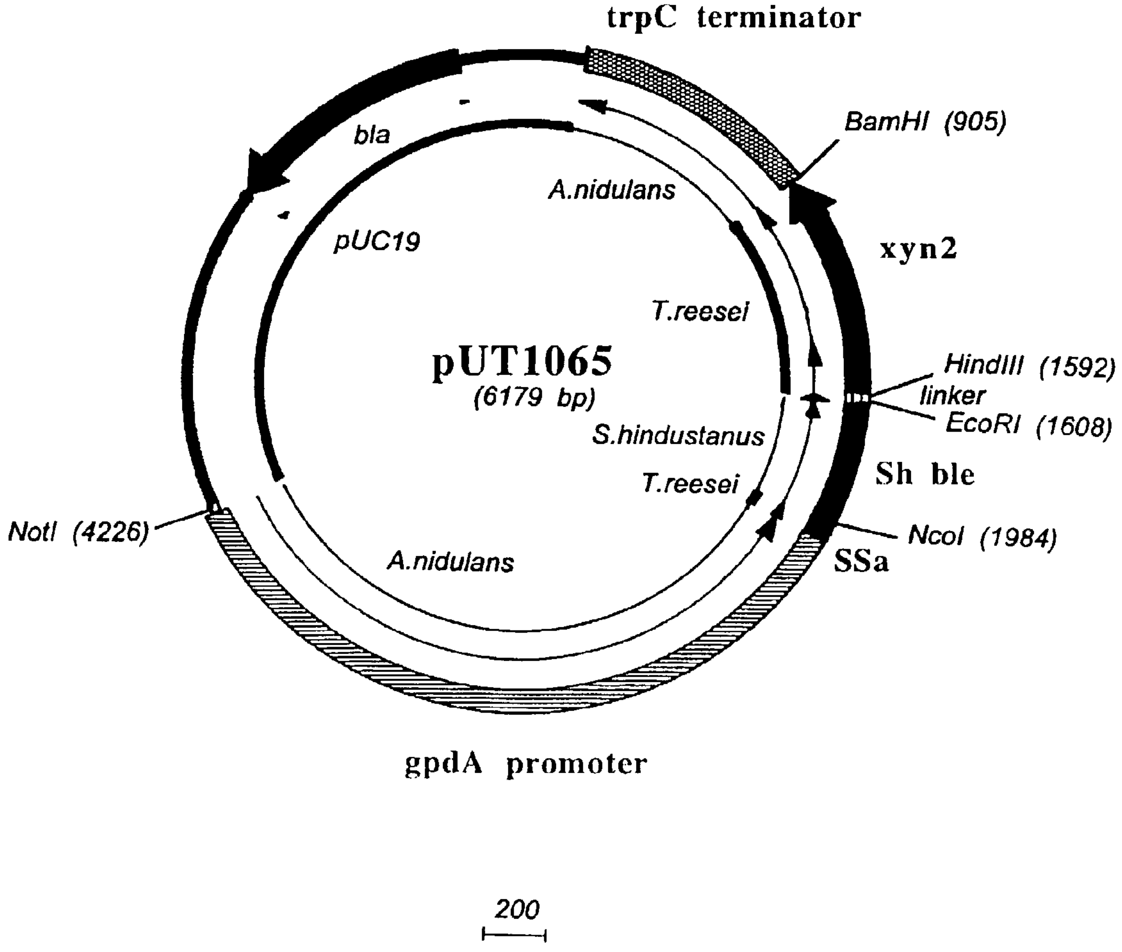
FIG. 2 is a pUT1065 map

1. Calmels T. P., Martin F., Durand H., and Tiraby G. (1991) *Proteolytic events in the processing of secreted proteins in fungi*. J Biotechnol 17(1): p. 51-66.
2. Punt P. J., Dingemanse M. A., Jacobs-Meijsing B. J., Pouwels P. H., and van den Hondel C. A. (1988) *Isolation and characterization of the glyceraldehyde-3-phosphate dehydrogenase gene of Aspergillus nidulans*. Gene 69(1): p. 49-57.
3. Shoemaker S., Schweickart V., Ladner M., Gelfand D., Kwok S., Myambo K., and Innis M. (1983) *Molecular cloning of exo-cellobiohydrolase I derived from Trichoderma reesei strain L27*. Bio/Technology October:691-696.
4. Drocourt D., Calmels T., Reynes J. P., Baron M., and Tiraby G. (1990) *Cassettes of the Streptoalloteichus hindustanus ble gene for transformation of lower and higher eukaryotes to phleomycin resistance*. Nucleic Acids Res 18(13): p. 4009.
5. Mullaney E. J., Hamer J. E., Roberti K. A., Yelton M. M., and Timberlake W. E. (1985) *Primary structure of the trpC gene from Aspergillus nidulans*. Mol Gen Genet 199(1): p. 37-45.
6. Yanisch-Perron C., Vieira J., and Messing J. (1987) *Improved M13 phage cloning vectors and host strains: nucleotide sequences of the M13mp18 and pUC19 vectors*. Gene 33:103-119.
7. Durand H., Baron M., Calmels T., and Tiraby G. (1988) *Classical and molecular genetics applied to Trichoderma reesei for the selection of improved cellulolytic industrial strains, in Biochemistry and genetics of cellulose degradation*, J. P. Aubert, Editor. Academic Press. p. 135-151.
8. Lowry O. H., Rosebrough N. J., Farr A. L., and Randall R. J. (1951) *Protein measurements with the folin phenol reagent*. J. Biol. Chem. 193: 265-275.
9. Parriche M., Bousson J. C., Baron M., and Tiraby G. *Development of heterologous protein secretion systems in filamentous fungi. in 3rd European Conference on Fungal Genetics*. 1996. Münster, Germany.
10. Baron M., Tiraby G., Calmels T., Parriche M., and Durand H. (1992) *Efficient secretion of human lysozyme fused to the Sh ble phleomycin resistance protein by the fungus Tolypocladium geodes*. J Biotechnol 24(3): p. 253-266.
11. Jeenes D. J., Marczinke B., MacKenzie D. A., and Archer D. B. (1993) *A truncated glucoamylase gene fusion for heterologous protein secretion from Aspergillus niger*. FEMS Microbiol. Lett. 107(2-3): p. 267-271.
12. Stone P. J., Makoff A. J., Parish J. H., and Radford A. (1993) *Cloning and sequence-analysis of the glucoamylase gene of neurospora-crassa*. Current Genetics 24(3): p. 205-211.
13. Mörsky P. (1983) *Turbidimetric determination of lysozyme with Micrococcus lysodeikticus cells: Reexamination of reaction conditions*. Analytical Biochem. 128: 77-85.
14. Paluh J. L., Orbach M. J., Legerton T. L., and Yanofsky C. (1988) *The cross-pathway control gene of Neurospora crassa, cpc-1, encodes a protein similar to GCN4 of yeast and the DNA-binding domain of the oncogene v-jun-encoded protein*. Proc. Natl. Acad. Sci. USA 85(11): p. 3728-32.
15. Nakari T., Onnela M. L., Ilmen M., Nevalainen K., and Penttilä M. (1994) *Fungal promoters active in the presence of glucose*, WO 94/04673, Alko.
16. Torronen A., Mach R. L., Messner R., Gonzalez R., Kalkkinen N., Harkki A., and Kubicek C. P. (1992) *The two major xylanases from Trichoderma reesei: characterization of both enzymes and genes*. Biotechnology (N Y) 10(11): p. 1461-5.
17. Farkas V. (1985) *Novel media for detection of microbial producers of cellulase and xylanase*. FEMS Microbiol. Letters 28:137-140.
18. Miller G. L. (1959) *Use of dinitrosalicylic acid reagent for determination of reducing sugar*. Anal. Chem. 31:426-428.
19. Punt P. J., Mattern I. E., van den Hondel C. A. M. J. J. (1988) *A vector for Aspergillus transformation conferring phleomycin resistance*. Fungal Genetics Newsletter 35, 25-30.

DNA sequence and amino acid of complete Chrysosporium CBH1 gene including promoter and terminator sequences. Promoter sequence (1-1779), terminator sequence (3427-4451) and intron sequence (2179-2256) are given in small case.

```
aaggtatccgatttggggaacgtcgatgaaagtattgcaaaagtgacgagagttgcgcaa    60   SEQ ID No. 1

ctaactcgctgccgaagaagctgcggaagaaagagaacaccgaaagtggaataacgttac   120

ggatgtcctgacctcaaagttgaaaccagcccttcctgctctatttgggaaagcggcttg   180

cccttgaatgcgctgcactgtggcacgactaccagtgatcgggaggagcaaactaccctg   240

gtccgttccttggtggggcggcactaggcccaacttagggtgatcggaggtcgatgccgc   300

ggtcctcgttggtctgggctcttctcatttcccggtttgcacccccgttgcacctgctg   360

atcgcccgccaacgccgatgaggttgcgcccagaccgacaatcaccgcggctgcattccc   420

aagtatattgaagatggcaccaggtacccggttttgcgtcccagtcgtttggtgccaaat   480

ttgggagtttttgagcctcaagatctggggaaatcgacctcaacttccatacaagttaaa   540

gtcgcacacacggcgagttccacgaagagacacatttttttctgaaggcctctctccccg   600

cacatcagaaaccaccaaataccaagactgcagaagccggggtaagtgggccaccgggac   660

tacactaaaatgcggggagaagcgagatccgttgcgaagggaagggatggggtgtgctgc   720

ggctttctccgctctcgtgcgccttttgcttgaatctagtgtacaccagggtaggctccg   780

aaggagtatctacggcagcgctgttcgtgctgcgttgagagtcagggcggagacgagcag   840

gcgacaggagcctcgcaccggcacttcggatcgcatttgcgcggagcgtcaaatacgctc   900

ttctgcggtcatcagagagcatcgtgaaccaaggttcttccgcagggcggcctgggcttc   960

gcagagtcgcactcggcggacgccttccgtgtcacccctgataacctggctgccgcgccc  1020

agactcctccaatgaggtgtgtggttgccctcgccgacccttcagcaaccttaatcgctt  1080

ccatcgcacggctccacgtcctcgaacgatgccctcagtccgtgcccggccgtggcaacc  1140

ataacgtgacatcgccgcccagcctactagccgctatcgaccggttaggcttgtcaccgc  1200

agcgcccattctccatcgggcctctactctgatccacctcacccaccgcaagcactagcg  1260

agcctcaccagagtgcaagcgacacgacccgcttggcccttcgtccttgactatctccca  1320

gacctcttgccatcttgccgacgccgccccctttttttttctcctcccctgccggcaggt  1380

cggtggccccagtcccgagatggcattgctccgttgtccatgacgacccatcattcgatg  1440

gctgactggcacactcgtcttgtttgagcatcgacggcccgcggcccgtctcccacggta  1500

cggaacctcgttgtacagtacctctcgtaatgatacccaacaccggggccgagcgctggg  1560

agggcggcgttcccgagaagccgggaaggcggctggccggctgacctttgtgacttggcg  1620

atggatgcggccatggagaatgtccgtccgaagcgacgcgacaattagcctggctaccat  1680

cgatataaattgggtgattcccagctcttgatgggcgtgtcttctgcctggcagccctcg  1740

tcttcagatcaagcaactgtgtgctgatcctcttccgccATGTACGCCAAGTTCGCGACC  1800
M Y A K F A T

CTCGCCGCCCTTGTGGCTGGCGCCGCTGCTCAGAACGCCTGCACTCTGACCGCTGAGAAC  1860
L A A L V A G A A A Q N A C T L T A E N

CACCCCTCGCTGACGTGGTCCAAGTGCACGTCTGGCGGCAGCTGCACCAGCGTCCAGGGT  1920
H P S L T W S K C T S G G S C T S V Q G

TCCATCACCATCGACGCCAACTGGCGGTGGACTCACCGGACCGATAGCGCCACCAACTGC  1980
S I T I D A N W R W T H R T D S A T N C

TACGAGGGCAACAAGTGGGATACTTCGTACTGCAGCGATGGTCCTTCTTGCGCCTCCAAG  2040
Y E G N K W D T S Y C S D G P S C A S K

TGCTGCATCGACGGCGCTGACTACTCGAGCACCTATGGCATCACCACGAGCGGTAACTCC  2100
C C I D G A D Y S S T Y G I T T S G N S
```

-continued

```
CTGAACCTCAAGTTCGTCACCAAGGGCCAGTACTCGACCAACATCGGCTCGCGTACCTAC  2160
L N L K F V T K G Q Y S T N I G S R T Y

CTGATGGAGAGCGACACCAAGTACCAGAgtaagttcctctcgcacccggccgccgggaga  2220
L M E S D T K Y Q M

tgatggcgcccagcccgctgacgcgaatgacacaGTGTTCCAGCTCCTCGGCAACGAGTT  2280
F Q L L G N E F

CACCTTCGATGTCGACGTCTCCAACCTCGGCTGCGGCCTCAATGGCGCCCTCTACTTCGT  2340
T F D V D V S N L G C G L N G A L Y F V

GTCCATGGATGCCGATGGTGGCATGTCCAAGTACTCGGGCAACAAGGCAGGTGCCAAGTA  2400
S M D A D G G M S K Y S G N K A G A K Y

CGGTACCGGCTACTGTGATTCTCAGTGCCCCCGCGACCTCAAGTTCATCAACGGCGAGGC  2460
G T G Y C D S Q C P R D L K F I N G E A

CAACGTAGAGAACTGGCAGAGCTCGACCAACGATGCCAACGCCGGCACGGGCAAGTACGG  2520
N V E N W Q S S T N D A N A G T G K Y G

CAGCTGCTGCTCCGAGATGGACGTCTGGGAGGCCAACAACATGGCCGCCGCCTTCACTCC  2580
S C C S E M D V W E A N N M A A A F T P

CCACCCTTGCACCGTGATCGGCCAGTCGCGCTGCGAGGGCGACTCGTGCGGCGGTACCTA  2640
H P C W V I G Q S R C E G D S C G G T Y

CAGCACCGACCGCTATGCCGGCATCTGCGACCCCGACGGATGCGACTTCAACTCGTACCG  2700
S T D R Y A G I C D P D G C D F N S Y R

CCAGGGCAACAAGACCTTCTACGGCAAGGGCATGACGGTCGACACGACCAAGAAGATCAC  2760
Q G N K T F Y G K G M T V D T T K K I T

GGTCGTCACCCAGTTCCTCAAGAACTCGGCCGGCGAGCTCTCCGAGATCAAGCGGTTCTA  2820
V V T Q F L K N S A G E L S E I K R F Y

CGTCCAGAACGGCAAGGTCATCCCCAACTCCGAGTCCACCATCCCGGGCGTCGAGGGCAA  2880
V Q N G K V I P N S E S T I P G V E G N

CTCCATCACCCAGGACTGGTGCGACCGCCAGAAGGCCGCCTTCGGCGACGTGACCGACTT  2940
S I T Q D W C D R Q K A A F G D V T D

NCAGGACAAGGGCGGCATGGTCCAGATGGGCAAGGCCCTCGCGGGGCCCATGGTCCTCGT  3000
Q D K G G M V Q M G K A L A G P M V L V

CATGTCCATCTGGGACGACCACGCCGTCAACATGCTCTGGCTCGACTCCACCTGGCCCAT  3060
M S I W D D H A V N M L W L D S T W P I

CGACGGCGCCGGCAAGCCGGGCGCCGAGCGCGGTGCCTGCCCCACCACCTCGGGCGTCCC  3120
D G A G K P G A E R G A C P T T S G V P

CGCTGAGGTCGAGGCCGAGGCCCCCAACTCCAACGTCATCTTCTCCAACATCCGCTTCGG  3180
A E V E A E A P N S N V I F S N I R F G

CCCCATCGGCTCCACCGTCTCCGGCCTGCCCGACGGCGGCAGCGGCAACCCCAACCCGCC  3240
P I G S T V S G L P D G G S G N P N P P

CGTCAGCTCGTCCACCCCGGTCCCCTCCTCGTCCACCACATCCTCCGGTTCCTCCGGCCC  3300
V S S S T P V P S S S T T S S G S S G P

GACTGGCGGCACGGGTGTCGCTAAGCACTATGAGCAATGCGGAGGAATCGGGTTCACTGG
T G G T G V A K H Y E Q C G G I G F T G

CCCTACCCAGTGCGAGAGCCCCTACACTTGCACCAAGCTGAATGACTGGTACTCGCAGTG  3420
P T Q C E S P Y T C T K L N D W Y S Q C

CCTGTAAacgaacctctctgaaggaggttctgagacacgcgcgattcttctgtatatagt  3480
L *

tttatttttcactctggagtgcttcgctccaccagtacataaaccttttttttcacgtaa  3540

caaaatggcttcttttcagaccatgtgaaccatcttgatgccttgacctcttcagttctc  3600

actttaacgtagttcgcgttagtctgtatgtcccagttgcatgtagttgagataaatacc  3660

cctggaagtgggtctgggcctttgtgggacggagccctctttctgtggtctggagagccc  3720

gctctctaccgcctaccttcttaccacagtacactactcacacattgctgaactgaccca  3780

tcataccgtactttatcctgttaattcgtggtgctgtcgactattctatttgctcaaatg  3840
```

-continued gagagcacattcatcggcgcagggatacacggtttatggaccccaagagtgtaaggacta 3900 ttattagtaatattatatgcctctaggcgccttaacttcaacaggcgagcactactaatc 3960 aacttttggtagacccaattacaaacgaccatacgtgccggaaattttgggattccgtcc 4020 gctctccccaaccaagctagaagaggcaacgaacagccaatcccggtgctaattaaatta 4080 tatggttcatttttttaaaaaaatttttcttcccattttcctctcgcttttctttttc 4140 gcatcgtagttgatcaaagtccaagtcaagcgagctatttgtgctatagctcggtggcta 4200 taatcagtacagcttagagaggctgtaaaggtatgataccacagcagtattcgcgctata 4260 agcggcactcctagactaattgttacggtctacagaagtaggtaataaaagcgttaattg 4320 ttctaaatactagaggcacttagagaagctatctaaatatatattgaccctagcttatta 4380 tccctattagtaagttagttagctctaacctatagatagccaaatgctataataggtacc 4440 agggttcaaaa 4451

Amino acid of complete Chrysosporium CBH1 protein. The putative signal peptide (1-19) is shown in italic letters and the cellulose binding domain (496-526) is shown in bold underlined letters.

*MYAKFATLAA LVAGAAAQNA* CTLTAENHPS LTWSKCTSGG SCTSVQGSIT 50 SEQ ID No: 2

IDANWRWTHR TDSATNCYEG NKWDTSYCSD GPSCASKCCI DGADYSSTYG 100

ITTSGNSLNL KFVTKGQYST NIGSRTYLME SDTKYQMFQL LGNEFTFDVD 150

VSNLGCGLNG ALYFVSMDAD GGMSKYSGNK AGAKYGTGYC DSQCPRDLKF 200

INGEANVENW QSSTNDANAG TGKYGSCCSE MDVWEANNMA AAFTPHPC V 250

IGQSRCEGDS CGGTYSTDRY AGICDPDGCD FNSYRQGNKT FYGKGMTVDT 300

TKKITVVTQF LKNSAGELSE IKRFYVQNGK VIPNSESTIP GVEGNSITQD 350

WCDRQKAAFG DVTD QDKGG MVQMGKALAG PMVLVMSIWD DHAVNMLWLD 400

STWPIDGAGK PGAERGACPT TSGVPAEVEA EAPNSNVIFS NIRFGPIGST 450

VSGLPDGGSG NPNPPVSSST PVPSSSTTSS GSSGPTGGTG VAKHYEQCGG 500
IGFTGPTQCE SPYTCTKLND WYSQCL* 526

DNA sequence sequence of complete Chrysosporium Xyl1 gene including promoter and terminator sequences. Promoter sequence (1-969), terminator sequence (2428-3030(3028)) and intron sequences (1043-1116, 1181-1332(1331), 1596(1595)-1674(1672) are given in small case.

tcatcaacttggcgtttggatgtactaatattacacgtcgtttgcnnagcggagtctgtg 60 SEQ ID No. 3 tcatctccgtggggtcgggtgctccagacgacgcttcgggccgatcctgaattcgggaag 120 gaaacggttcggctaatcaggtcctctaaaatataacgaagcactacagagggagttcct 180 cagaggacatcgtatcaaccgaagaacgaagcgccgaaaggactgatcaaaacaggagta 240 ggtagggatgtgtgagtacctaaactttccatacctgacataaaatcatcatggtgcttc 300 agacctgtttgatgaggcgagggcggaggccgcattgtattttcgttccttccttctttt 360 tgttagtatatctnagggttccatcgtaaaatggaatcttccagctctactagtaattag 420 aacaatagttctgatgtcgtgcgccaagctttttcagatgactgccaaaaacccatcatg 480 ggtatggacaaaagcagtaatcggagtcacaacgccgcattttccttcatgatttccgtc 540 aaccggagaggtcggaggaggactccggccacatgtgatgcgaagaagtacatggcgcca 600 tggttctaacctcttatagtctgaaaatgcgcggaggccagcgaagccaagcccgggaac 660 cgttcttgtcatggtttcagtattgtttcgctaaacattctatccgattcgcgataggtg 720 cggctgccaccgaaggttgtatccttaaagctttggtaagtacggagtacggaaatggaa 780 acgcgccgcagtcctggttccatcggtatcctccgcatgctccgccaaaaaaagaaaacc 840 cgggtatgtttacaaaggatataagagacaagatgcaccacccgccccttcccatctgc 900

-continued

```
cggttgcccacgtcgccgtcgactgcttgtccgcttcctacctgcagcctctttcagaga   960

ccatcaaacATGCGTACTCTTACGTTCGTGCTGGCAGCCGCCCCGGTGGCTGTGCTTGCC  1020
M R T L T F V L A A A P V A V L A

CAATCTCCTCTGTGGGGCCAGTgtatgtaattgccttactcggaaaatagtcaccactag  1080

agggacttaagctcactacttcctgtttcacaatagGCGGCGGTCAAGGCTGGACAGGTC  1140
G G Q G W T G

CCACGACCTGCGTTTCtGGCGCAGTATGCCAATTCGTCAAgtcagtaactgcttttatt   1200
P T T C V S G A V C Q F V N

tcttttctctctgggattacgatttcgttttgcacttagcttggttctgcatttcattgt  1260

tgtattgttctctttttgtgtgtgagaggttttattaccacctaaaggccatttgctaac  1320

aaatctccccagTGACTGGTACTCCCAATGCGTGCCCGGATCGAGCAACCCTCCTACGGG  1380
D W Y S Q C V P G S S N P P T G

CACCACCAGCAGCACCACTGGAAGCACCCCGGCTCCTACTGGCGGCGGCGGCAGCGGAAC  1440
T T S S T T G S T P A P T G G G G S G T

CGGCCTCCACGACAAATTCAAGGCCAAGGGCAAGCTCTACTTCGGAACCGAGATCGATCA  1500
G L H D K F K A K G K L Y F G T E I D H

CTACCATCTCAACAACAATGCCTTGACCAACATTGTCAAGAAAGACTTTGGTCAAGTCAC  1560
Y H L N N N A L T N I V K K D F G Q V T

TCACGAGAACAGCTTGAAGTGGGATGCTACTGAGCgtgagtgacctctcctccttctccc  1620
H E N S L K W D A T E P

gacaataatagataattacgagccggttcgaggctgacattgcgcgattctagCGAGCC   1680
S R

GCAATCAATTCAACTTTGCCAACGCCGACGCGGTTGTCAACTTTGCCCAGGCCAACGGCA  1740
N Q F N F A N A D A V V N F A Q A N G K

AGCTCATCCGCGGCCACACCCTCCTCTGGCACTCTCAGCTGCCGCAGTGGGTGCAGAACA  1800
L I R G H T L L W H S Q L P Q W V Q N I

TCAACGACCGCAACACCTTGACCCAGGTCATCGAGAACCACGTCACCACCCTTGTCACTC  1860
N D R N T L T Q V I E N H V T T L V T R

GCTACAAGGGCAAGATCCTCCACTGGGACGTCGTTAACGAGATCTTTGCCGAGGACGGCT  1920
Y K G K I L H W D V V N E I F A E D G S

CGCTCCGCGACAGCGTCTTCAGCCGCGTCCTCGGCGAGGACTTTGTCGGCATCGCCTTCC  1980
L R D S V F S R V L G E D F V G I A F R

GCGCCGCCCGCGCCGCCGATCCCAACGCCAAGCTCTACATCAACGACTACAACCTCGACA  2040
A A R A A D P N A K L Y I N D Y N L D I

TTGCCAACTACGCCAAGGTGACCCGGGGCATGGTCGAGAAGGTCAACAAGTGGATCGCCC  2100
A N Y A K V T R G M V E K V N K W I A Q

AGGGCATCCCGATCGACGGCATCGGCACCCAGTGCCACCTGGCCGGGCCCGGCGGGTGGA  2160
G I P I D G I G T Q C H L A G P G G W N

ACACGGCCGCCGGCGTCCCCGACGCCCTCAAGGCCCTCGCCGCGGCCAACGTCAAGGAGA  2220
T A A G V P D A L K A L A A A N V K E I

TCGCCATCACCGAGCTCGACATCGCCGGCGCCTCCGCCAACGACTACCTCACCGTCATGA  2280
A I T E L D I A G A S A N D Y L T V M N

ACGCCTGCCTCCAGGTCTCCAAGTGCGTCGGCATCACCGTCTGGGGCGTCTCTGACAAGG  2340
A C L Q V S K C V G I T V W G V S D K D

ACAGCTGGAGGTCGAGCAGCAACCCGCTCCTCTTCGACAGCAACTACCAGCCAAAGGCGG  2400
S W R S S S N P L L F D S N Y Q P K A A

CATACAATGCTCTGATTAATGCCTTGTAAgaggaggtatattatttttagaggcaatgaa  2460
Y N A L I N A L *

gctaggaggaaagaggggaagtgaggtaattagctaggacaggcaaatctagcagcaatt  2520

ataagtcaacactatataaaatattcctataatggcttgtgcttcggtgtgcaaaaaaaa  2580

aaaaaaaaaaaaaaaaaaaaaaaaaaaaaaaactcaaaaacaaaaatgatccaacatgatt  2640

cgaaatggcgaccttgcaaatgcacacctcagataataccactatacaatacaccttaaa  2700
```

-continued tggcacctaaatccatttgtctgcggtcatagacggggcttaagaagcctgggatgcagg 2760 tgtcgatgcaagggttacgtcagtgtatgatatgagtatgaaccatgctgtctgggtaat 2820 tctccactttccctccccttacgactcttcgggtgtgcctctctagaaagtcgactcctg 2880 gcgcctcagatcgccctttggctctgttcggtacaatgacgtccgctggtttcttccaaa 2940 gaccaggtatttctcccgtggcaacaaagaataccaaatacctatatcgaaccgtagtct 3000 tctgataattagatgtctctcaaggcgcgg 3030

Amino acid sequence of complete Chrysosporium Xyl1 protein. The signal peptide (1-20) is shown in italic letters and the cellulose binding domain (22-53) is shown in bold underlined letters.

1 *MRTLTFVLAA APVAVLAQSP* LWGQCGGQGW TGPTTCVSGA VCQFVNDWYS SEQ ID No. 4

51 QCVPGSSNPP TGTTSSTTGS TPAPTGGGGS GTGLHDKFKA KGKLYFGTEI

101 DHYHLNNNAL TNIVKKDFGQ VTHENSLKWD ATEPSRNQFN FANADAVVNF

151 AQANGKLIRG HTLLWHSQLP GWVQNINDRN TLTQVIENHV TTLVTRYKGK

201 ILHWDVVNEI FAEDGSLRDS VFSRVLGEDF VGIAFRAARA ADPNAKLYIN

251 DYNLDIANYA KVTRGMVEKV NKWIAQGIPI DGIGTQCHLA GPGGWNTAAG

301 VPDALKALAA ANVKEIAITE LDIAGASAND YLTVMNACLQ VSKCVGITVW

351 GVSDKDSWRS SSNPLLFDSN YQPKAAYNAL INAL*

DNA sequence of partial Chrysosporium GPD1 gene including promoter sequences. Promoter sequence (1-1555) and intron sequence (1682-1781) are given in small case. The 3' end of the gene is lacking.

tgagcagcaatgagcagcaatgagcattcctgggccaccgagtctgagtgccagtacgga 60 SEQ ID No: 5 gtatcgtacttcgtaccggggtttgatttggtgacggtgcttttcacctctcgatgcccg 120 aaatcgggtctaagctgagtttgatcaaatatgtgactccaacatcgccccccttcggcaa 180 accccgtcgacacgtgtgtcatccttccattgcaagcgatcactcgcagggcgtgacgat 240 gaacgagattttttgcccggaccgattcgcggatatagcggcagccgaccagccctaccac 300 actgatggccgtgtcactagtgtatgctcccagaaccgcaagcatacactgggcaatgct 360 tggtatgcagttgaggcagctttatgtttccatacccttccacttcggctcggggactcg 420 gcggggtcgcggaagtttgacggcagccgtcgggccttaggccgagattaccgtggttgt 480 ggcccagttttagccgttcccgtccgtttcctaccggaccatgattttcgtgaaccattg 540 caatcccgaagcgcatttccgacgttaaggagttacctccgctgcccagaattcatgatc 600 gtggccggctcaaggcagcgtggcggggcatccgtgtcaagctcccaggaggaggtgcgc 660 gatttcaaatccgggccaaaacaggccaagactggctggccaaaaaaaggagcgtagacg 720 gcccgggacatcggacgtcagctcgcagccacccaaaaccggtccgatctactcgcttac 780 tgtggtagttcaggtacttttgagtagtaaaaacgctacggcagggccgggggggttcccc 840 ggtgacggaggtgcctctgcggtggcgaacatcccacgcactctcgagctacggtgacac 900 ctcgtgtcctgttggtcttgcaatgctggggcggcaggaaatgcgtcgcgctcctcccgg 960 ccaagacctaaaacagacagcgccgcaaagtcgctcactagcaccgcgaaacgaagatgc 1020 cccacctcaacgcaatctgtgatgcaagcaattgggaaggctcaccccacctcagcgagg 1080 ggctcaaccattttttattatcagctcatgccaccacaacatgactgttttctttccttgc 1140 tcatcccacatttgacaaaaatcgtcgattaatctctttccatacaggccgtccgcgctc 1200 tgataaccacataaaagtctcttcagtcaacagctcaaagctccctcatccctccaggta 1260 agcagccaaagagctcccccacggaccccgcactgcctcatcccgcctgtatcggacctg 1320 cgcgacccagcagagaatcccaaacctttgctgcttgctgcccggttccggactgagctg 1380

-continued caacccaagcctttaaaaagcttttcccttctcccacggtgtcaactctgtcctatccct 1440 ccgacatccgttgagctcaacaactccccgaaccttttaccccgcgccgagctacccctc 1500 catcaaaccaccctgacagctcgctcactcacctccccacatcacagaaatcaaaATGAC 1560
M T -

TATCAAGGTCGGCATCAACGGTTTCGGCCGTATCGGCCGTATCGTCTTCCGCAACTCCAT 1620
I K V G I N G F G R I G R I V F R N S I -

CGAGCACTCGGATGTCGAGATCGTTGCCGTCAACGACCCCTTCATTGAGCCCAAGTACGC 1680
E H S D V E I V A V N D P F I E P K Y A -

Tgtaagtagtttttttttccttcctcgcgttctttcctgttccatcgacagtacgagat 1740

GatcttgcaggcggatcggagctaaccgcgattgtcgtacagGAGTACATGCTCAAGTAT 1800
E Y M L K Y -

GACTCGACCCACGGTATCTTCAACGGCACCATCGCCGTCGAGGGCAACGACCTCATTGTC 1860
D S T H G I F N G T I A V E G N D L I V -

AACGGCAAGAGGGTCAAGTTCTACACTGAGCGGGMCCCCGCCAACATTCCCTGGARGGAA 1920
N G K R V K F Y T E R P A N I P W E -

ACTGGTGCCGAGTACATMRTCGAGTCGACCGGTGTGTTCACCAMCACCSAGAAGGCTAGC 1980
T G A E Y I E S T G V F T T K A S -

GCCCACCTCAAGGGCGGCGCCAAGCGCGTCATCATCTCTGCTCCCTCGGCCGATGCCCCC 2040
A H L K G G A K R V I I S A P S A D A P -

ATGTACGTCATGGGCGTCAACGAGAAGACCTACGACGGCAAGGCCCAGGTCATCTCTAAC 2100
M Y V M G V N E K T Y D G K A Q V I S N -

GCCTCGTGCACCACCAACTGCCTGGCTCCCCTCGCCAAGGTCATCCACGACAAGTTCGGC 2160
A S C T T N C L A P L A K V I H D K F G -

CTCGTTGAGGGTCTCATGACCACCGTCCACTCCTACACTGCCACCCAGAAGACCGTCGAT 2220
L V E G L M T T V H S Y T A T Q K T V D -

GGTCCCTCTGCCAAGGACTGGCGTGGTGGCCGTGGTGCTGCTCAGAACATCATCCCCAGC 2280
G P S A K D W R G G R G A A Q N I I P S -

AGCACTGGCGCCGCCAAGGCCGTCGGCAAGGTCATCCCTGAGCTCAACGGCAAGCTCACC 2340
S T G A A K A V G K V I P E L N G K L T -

GGCATGTCCCTCCGTGTCCCCACCCCCAACGTTTCCGTTGTCGACCTCACCTGCCGCCTC 2400
G M S L R V P T P N V S V V D L T C R L -

GAGAAGGAGCCTACCTACGACGACATCAAGGCCGCCATCAAGGAGGCCGCCGCCGGCCCC 2460
E K E A T Y D D I K A A I K E A A A G P -
CTCAAGGgtgagttatctggttcctttttttttttttggagaacgacacatgctgataaa 2520
L K G acccagGCATCCTCGACTACACTGAGG 2547
I L D Y T E Amino acid of partial Chrysosporium GPD1 protein (the C-terminus is lacking in the sequence available).
MTIKVGINGF GRIGRIVFRN SIEHSDVEIV AVNDPFIEPK YAEYMLKYDS SEQ ID No. 6

THGIFNGTIA VEGNDLIVNG KRVKFYTER PANIPW ETC AEYI ESTGV

FT T KASAH LKGGAKRVII SAPSADAPMY VMGVNEKTYD GKAQVISNAS

CTTNCLAPLA KVIHDKFGLV EGLMTTVHSY TATQKTVDGP SAKDWRGGRG

AAQNIIPSST GAAKAVGKVI PELNGKLTGM SLRVPTPNVS VVDLTCRLEK

EATYDDIKAA IKEAAAGPLK GILDYTE

The invention claimed is:

1. An isolated functional family 10 glycosyl hydrolase having β-xylanase activity from *Chrysosporium* comprising an amino acid sequence identical to the amino acid sequence at positions 1-384 of SEQ ID No. 4, with the proviso that the amino acid at position 44 of SEQ ID No. 4 is F, W or Y.

2. An isolated functional family 10 glycosyl hydrolase comprising the amino acid sequence set forth in SEQ ID No. 4.

3. An isolated functional family 10 glycosyl hydrolase having β-xylanase activity from *Chrysosporium* comprising the sequence of amino acids from position 54 through position 384 of SEQ ID No. 4.

4. The glycosyl hydrolase from claim 3 further comprising the sequence of amino acids from position 22 through position 53 of SEQ ID No. 4.

5. The isolated glycosyl hydrolase of claim 3 wherein the signal peptide is absent.

6. The isolated glycosyl hydrolase of claim 3 wherein the cellulose binding domain is absent.

7. An isolated functional family 10 glycosyl hydrolase having β-xylanase activity from *Chrysosporium* comprising an amino acid sequence identical to the amino acid sequence at positions 22-384 of SEQ ID No. 4, with the proviso that the amino acid at position 44 of SEQ ID No. 4 is F, W or Y.

8. A process of hydrolysing β-xylosidic bonds, comprising contacting a substrate having a β-xylosidic bond with a glycosyl hydrolase according to claim 2, 1, 3, 4 or 7 for a sufficient period of time for hydrolysis of the β-xylosidic bonds.

9. An isolated nucleic acid sequence encoding a glycosyl hydrolase according to claim 2, 1, 3, 4, or 7.

* * * * *